(12) United States Patent
Taniguchi et al.

(10) Patent No.: US 6,747,010 B2
(45) Date of Patent: *Jun. 8, 2004

(54) NKT CELL-ACTIVATING AGENTS CONTAINING α-GLYCOSYLCERAMIDES

(75) Inventors: Masaru Taniguchi, Chiba (JP); Tetsu Kawano, Chiba (JP); Yasuhiko Koezuka, Gunma (JP)

(73) Assignee: Kirin Beer Kabushiki Kaisha, Tokyo (JP)

(*) Notice: Subject to any disclaimer, the term of this patent is extended or adjusted under 35 U.S.C. 154(b) by 2 days.

This patent is subject to a terminal disclaimer.

(21) Appl. No.: 10/334,861

(22) Filed: Jan. 2, 2003

(65) Prior Publication Data

US 2003/0139351 A1 Jul. 24, 2003

Related U.S. Application Data

(62) Division of application No. 09/402,785, filed as application No. PCT/JP98/01657 on Apr. 10, 1998, now Pat. No. 6,531,453.

(30) Foreign Application Priority Data

Apr. 10, 1997 (JP) ................................. 9-92412

(51) Int. Cl.$^7$ .................. A61K 31/7028; A61K 31/715; C12N 5/08
(52) U.S. Cl. ................. 514/25; 514/61; 536/17.9; 536/18.7; 424/93.71; 424/579; 424/580; 435/372
(58) Field of Search ................ 514/25, 61; 536/17.9, 536/18.7; 424/93.71, 579, 580; 435/372

(56) References Cited

U.S. PATENT DOCUMENTS 5,767,092 A 6/1998 Koezuka et al.
5,780,441 A 7/1998 Higa et al.
6,531,453 B1 * 3/2003 Taniguchi et al. ............ 514/25

FOREIGN PATENT DOCUMENTS

| EP | 666268 | 8/1995 |
| EP | 0 957 161 A1 | 11/1999 |
| WO | WO 92/19633 A1 | 11/1992 |
| WO | WO 94/244142 | 10/1994 |

OTHER PUBLICATIONS

Cutting Edge, C. Camaud, et al., "Cross-Talk Between Cells of the Innate Immune System: NKT Cell Rapidly Activate NK Cell", pp. 4647–4560 (1999).
SCIENCE, T. Kawano, et al., CD1d-Restricted and TCR-Mediated Activation of Vα14 NKT Cells by Glycosylceramides, pp. 1626–1629, vol. 278, (Nov. 28, 1997).

(List continued on next page.)

Primary Examiner—James O. Wilson
Assistant Examiner—Devesh Khare
(74) Attorney, Agent, or Firm—Foley & Lardner

(57) ABSTRACT

An objective of the present invention is to provide NKT cell-activating agents, therapeutic agents for autoimmune diseases (for example, systemic lupus erythematosus, systemic sclerosis, ulcerative colitis, encephalomyelitis, multiple sclerosis and human type I diabetes), and abortifacients. The medicinal compositions according to the present invention comprise α-glycosylceramides of the following formula (I), or a salt or a solvate thereof as an active ingredient.

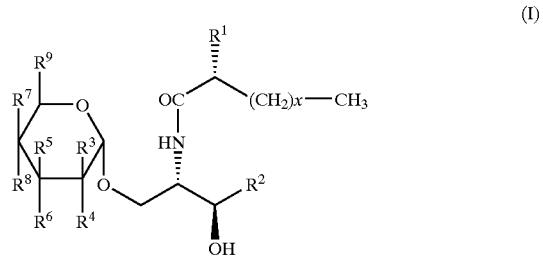

30 Claims, 12 Drawing Sheets

OTHER PUBLICATIONS

Proc. Natl. Acad. Sci. USA, T. Kawano et al., Natural killer–like nonspecific tumor cell lysis mediated by specific ligand–activated Vα14 NKT cells, vol. 95, pp. 5690–5693 (5/1998).

Hashimoto, W. et al. "Cytotoxic NK1.1 Ag+alpha–beta T cells with intermediate TCR induced in the liver of mice by IL–12" 1995, J. Immunol. vol. 154, pp. 4333–4340.

Morita, M. et al. "Syntheses of alpha– and beta–monoglycosylceramides . . . " Bioorg. & Med. Chem Lett. vol. 5, No. 7, pp 699–704, 1995.

Koyobashi, et al., "Enhancing Effects of Agelasphin–11 on Natural Killer Cell Activities of Normal and Tumor–Bearing Mice," Biol. Pharm. Bull., vol. 19, No. 3, 350–353 (1996).

Motoki, et al. "Effects of α–Galactosylceramides on Bone Marrow Cells in Vitro and Hematopoisis in Vivo," Biol. Pharm. Bull., vol. 19, No. 7, 952–955 (1995).

Kobayashi, et al., "KRN7000, A Novel Immunomodulator, and its Antitumor Activities," Oncology Research, vol. 7, No. 10/11, 529–534 (1995).

Sumida et al., "Selective Reduction of T Cells Bearing Invariant Vα24JαQ Antigen Receptor in Patients with Systemic Sclerosis," J. Exp. Med. (1995), vol. 182, pp. 1163–1167, XP002104249.

Van Der Vliet et al., "Effects of α–galactosylceramide (KRN7000), interleukin–12 and interleukin–7 on phenotype and cytokine profile of human Vα24+Vβ11+cells," Immunology (Dec. 1999), vol. 98, No. 4, pp. 557–563, XP008019160, ISSN: 0019–2805.

Mieza et al., "Selective Reduction of Vα14+NK T Cells Associated with Disease Development in Autoimmune–Prone Mice," Journal of Immunology (1996), vol. 156, pp. 4035–4040, XP001159198.

Hoshi et al., "KRN–7000: Immunostimulant," Drugs of the Future (1996), vol. 21, No. 2, pp. 152–154, XP008019158.

Motoki et al., "Antitumor Activities of Combined Treatment with a Novel Immunomodulator, (2S,3S,4R)–1–O–(α–D–Galactopyranosyl)–2–(N–Hexacosanoylamino)–1,3,4–Octadecanetriol (KRN7000), and Radiotherapy in Tumor Bearing Mice," Oncology Research (1996), vol. 8, No. 4, pp. 155–162, XP008019198, ISSN: 0965–0407.

Database CA 'Online!, Chemical Abstracts Service, Columbus, Ohio, US, Hasegawa, Akira et al: "Preparation of glycolipids," retrieved from STN Databse accession No. 122:240344 HCA XP002246441 *abstract* & JP 06 199884 A (Nisshin Oil Mills Ltd., Japan Hasegawa Akira) Jul. 19, 1994.

Database CA 'Online!, Chemical Abstracts Service, Columbus, Ohio, US, Matsushima, AmijiI et al: "TNF–.alpha. formation inhibitors containing sulfatide for autoimmune disease, inflammation and allergy," retrieved from STN Database accession No. 128:235130 HCA XP002246442 *abstract* & JP 10 045603 A (Yoshitomi Pharmaceutical Industries, Ltd., Japan) Feb. 17, 1998.

* cited by examiner

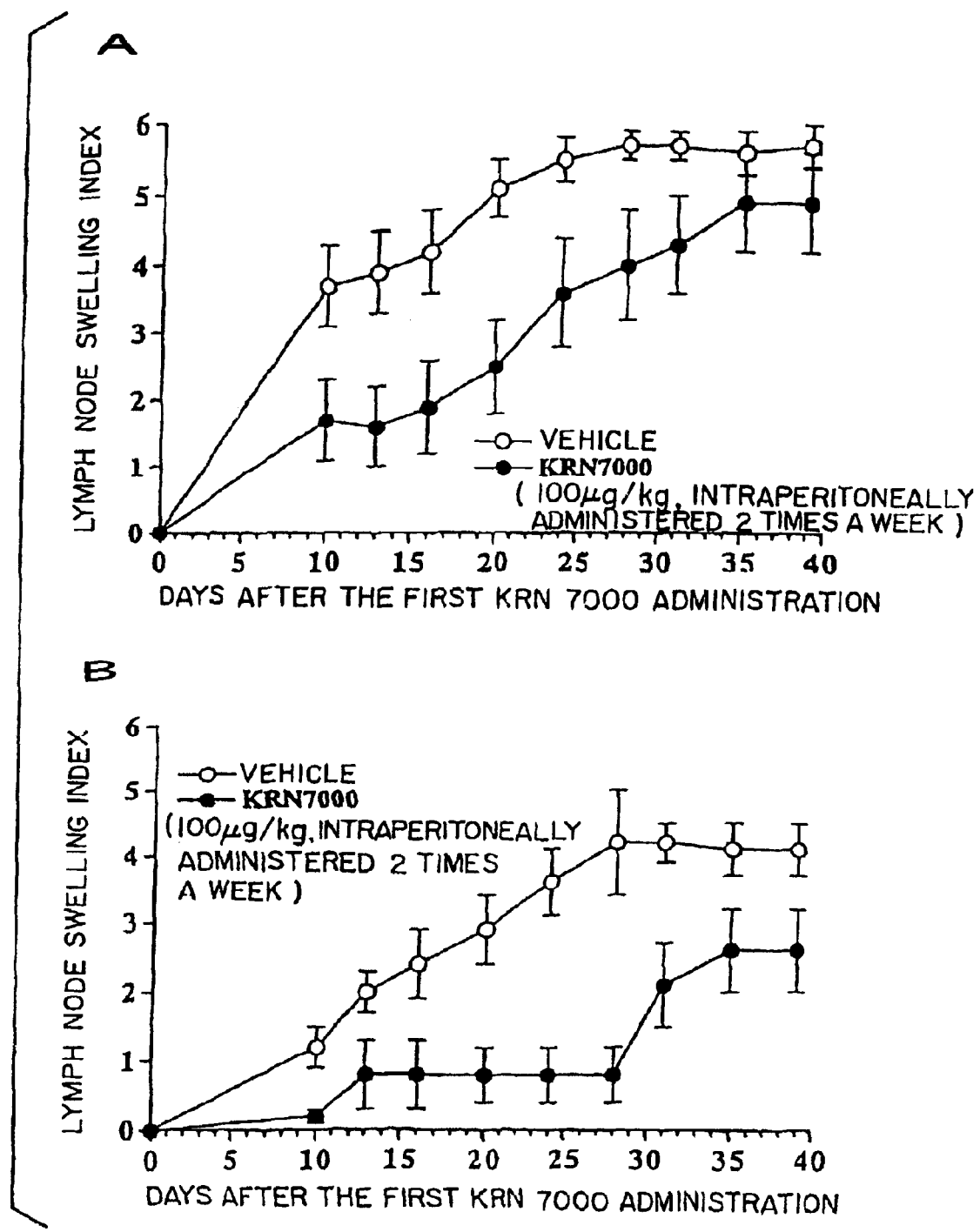
F I G. 3

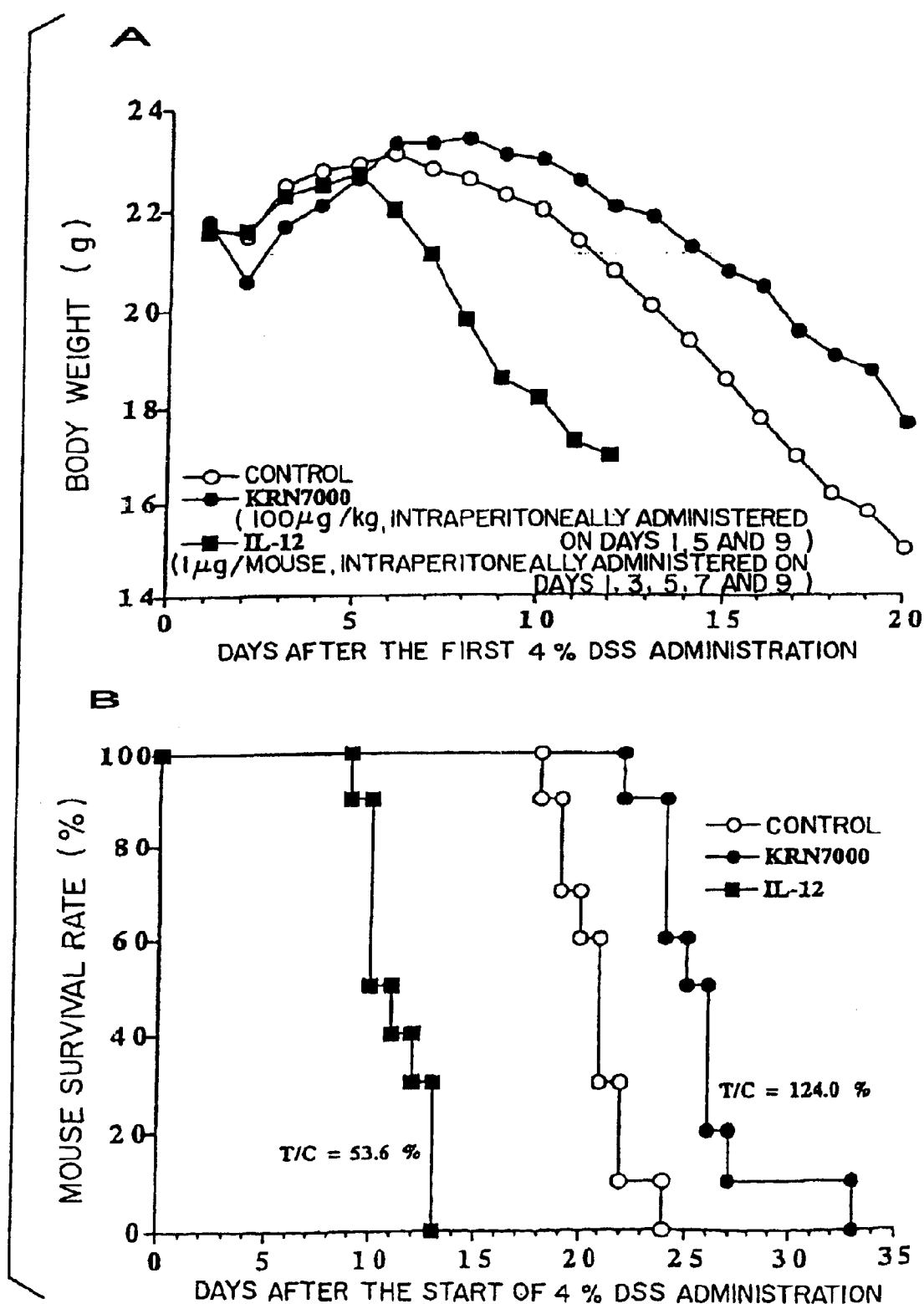
F I G. 5

NKT CELL-ACTIVATING AGENTS CONTAINING α-GLYCOSYLCERAMIDES

BACKGROUND OF THE INVENTION

1. Field of the Invention

The present invention relates to NKT cell-activating agents, therapeutic agents for autoimmune diseases and agents for inducing abortion.

2. Background Art

It has been revealed that intermediate TCR cells ($TCR^{int}$ cells), which express T-cell receptors (TCRs) intermediately, are related to natural killer (NK) cells in terms of their features, for example, showing a large granular lymphocyte (LGL)-like morphology, constantly expressing IL-2R β-chains, and having perforin granules, but they are clearly different from NK cells in terms of having TCRs (Watanabe, H. et al., J. Immunol., 155, 2972 (1995)). Furthermore, among the $TCR^{int}$ cells activated by interleukin 12 (IL-12), NK 1.1-expressing NK $1.1^{+}TCR^{int}$ (NKT) cells have been shown to be important effector cells in controlling hematogenous metastases of tumors to the liver and lung in mice (Hashimoto, W. et al., J. Immunol., 154, 4333 (1995); Anzai, R. et al., Immunol., 88, 82 (1996)). These data suggest that the NKT cells may play an important role in eradicating cancer cells, parasites, protozoans, and intracellular infectious bacteria such as *Listeria monocytogenes* and *Micobacterium tubeculosis* (Seki, S. et al., Clin. Immunol., 28, 1069 (1996)).

The NKT cells are also known to be closely associated with acute rejection in bone marrow transplantation (Yankelevich, B. et al., J. Immunol., 142, 3423 (1989)) and with controlling of IgE antibody production by controlling Th1/Th2 differentiation of helper T cells (Yoshimoto, T. et al., J. Exp. Med., 179, 1285 (1994)). Thus, the NKT cells are a group of new cells that are currently attracting enormous attention.

$Vα14^{+}$ NKT cells are a subset of the above-mentioned NKT cells. Many $Vα14^{+}$ NKT cells express Vα14Jα281 mRNA and have this as a TCR α-chain. Recently, the $Vα14^{+}$ NKT cells were shown to be closely associated with the onset of autoimmune diseases. The number of $Vα14^{+}$ NKT cells was revealed to selectively decrease prior to the onset of an autoimmune disease in MRL 1pr/1pr mice, model mice for an autoimmune disease (human systemic lupus erythematosus) in which abnormal lymphocytes accumulate at 17–20 weeks old (Mieza, M. A. et al., J. Immunol., 156, 4035 (1996)).

Similar phenomena were also observed in model mice for other autoimmune diseases, such as gld mice and (NZB× NZW) F1 mice, revealing that the $Vα14^{+}$ NKT cells are closely associated with the onset of autoimmune diseases (Makino, Y. et al., Clin. Immunol., 28, 1487 (1996)).

More interestingly, similar phenomena were also observed in humans. The Vα24JαQα chain, a human homologue to the mouse Vα14Jα281 chain, was found in peripheral blood $CD4^{-}/CD8^{-}$ T cells at a level of 20–50% in healthy humans but not at all in sclerosis patients (Sumida, T. et al., J. Exp. Med., 182, 1163 (1995)).

Thus, the mouse $Vα14^{+}$ NKT cells and human Vα24JαQα T cells are known to be involved in various autoimmune diseases which are caused by different causative genes or genetic background. Therefore, IL-12 having an NKT cell-activating activity as mentioned above was expected to be a therapeutic agent for autoimmune diseases such as human systemic lupus erythematosus (SLE) and systemic sclerosis (SSc). However, a marked increase in the number of abnormal lymphocytes ($CD3^{+}B220^{+}$ double negative T cells) in the spleen and lymph nodes was observed in MRL 1pr/1pr mice to which IL-12 was administered as compared with the control mice (Takenori Tsutsui et al., Proceedings of Annual Meeting of the Japanese Society for Immunology, 347 (1996)).

β-Galactosylceramides or β-glucosylceramides, in which various sugars bound to ceramides in a β-configuration, are present in the mammal body (Svennerholm, L. et al., Biochim. Biophys. Acta, 280, 626 (1972); Karlsson, K. -A. et al., Biochim. Biophys. Acta, 316, 317 (1973)). On the other hand, it is known that α-galactosylceramides have marked immunostimulatory activity and antitumor activity (Morita, M. et al., J. Med. Chem., 38, 2176 (1995)) and such activities by α-galactosylceramides or α-glucosylceramides are known to be much stronger than those by β-galactosylceramides or β-glucosylceramides (Motoki, K. et al., Biol. Pharm. Bull., 18, 1487 (1995)). It is also known that administration of compounds having an α-glucosylceramide structure protects the body from radiation (Motoki, K. et al., Bioorg. Med. Chem. Lett., 5, 2413 (1995)), suppresses the metastasis of mouse melanoma B16 to the lung (Kobayashi, E. et al., Oncology Res., 7, 529 (1995)) and metastasis of mouse colon adenocarcinoma, Colon 26, and mouse T lymphoma EL-4 to the liver (Kazuhiro Motoki et al., Proceedings of Annual Meeting of the Japanese Cancer Association, 523 (1996)), and increases the number of platelets and leukocytes (Motoki, K. et al., Biol. Pharm. Bull., 19, 952 (1996)).

However, there are no reports to date that compounds having an α-glucosylceramide structure are effective on autoimmune diseases, that such compounds would induce abortion, or that such compounds could even affect NKT cells.

SUMMARY OF THE INVENTION

The present inventors have now found that α-glycosylceramides enhance antitumor cytotoxic activity against tumor cells of NKT cells in RAG-1KO/Vα14tg/Vβ8.2tg mice (mice having a large number of NKT cells but neither B cells, T cells nor NK cells in the lymphocyte fraction), markedly increase the number of NKT cells, in particular, mouse $Vα14^{+}$ NKT cells and human $Vα24^{+}$ NKT cells, suppress abnormal swelling of axillary and inguinal lymph nodes (accumulation of abnormal lymphocytes) in MRL 1pr/1pr mice which are considered model mice for human systemic lupus erythematosus, and control the progression of mouse colitis induced with 4% DSS.

The present inventors have also found that α-glycosylceramides suppress the onset of experimental autoimmune encephalomyelitis. This experimental autoimmune encephalomyelitis in mice is a model for human multiple sclerosis. The present inventors have also found that α-glycosylceramides suppress the spontaneous onset of diabetes in NOD mice which are model animals for human type I diabetes.

The present inventors have further found that α-glycosylceramides have an aborting effect on pregnant mice.

An objective of the present invention is to provide an agent for activating an NKT cell and an activated NKT cell.

Another objective of the present invention is to provide a therapeutic agent for autoimmune diseases such as systemic lupus erythematosus, systemic sclerosis, ulcerative colitis, encephalomyelitis, multiple sclerosis, or type I diabetes.

Further objective of the present invention is to provide an agent for inducing abortion.

The NKT cell-activating agent, the therapeutic agent for autoimmune diseases and the agent for inducing abortion according to the present invention comprise a compound of formula (I) or a salt or a solvate thereof:

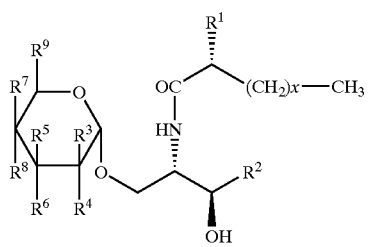

(I)

wherein $R^1$ represents H or OH,

X represents an integer between 7 and 27, $R^2$ represents a substituent selected from the group consisting of the following (a) to (e) (wherein Y represents an integer between 5 and 17):
(a) —$CH_2(CH_2)_YCH_3$
(b) —$CH(OH)(CH_2)_YCH_3$
(c) —$CH(OH)(CH_2)_YCH(CH_3)_2$
(d) —$CH=CH(CH_2)_YCH_3$
(e) —$CH(OH)(CH_2)_YCH(CH_3)CH_2CH_3$, and $R^3$ to $R^9$ represent substituents as defined in any one of the following i) to v):

i) when $R^3$, $R^6$ and $R^8$ represent H, $R^4$ represents H, OH, $NH_2$, $NHCOCH_3$, or a substituent selected from the group consisting of the following groups (A) to (D):

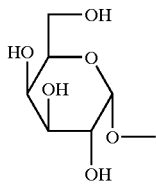

(A)

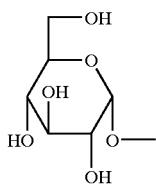

(B)

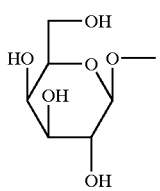

(C)

-continued

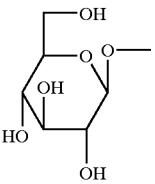

(D)

$R^5$ represents OH or a substituent selected from the group consisting of the following groups (E) and (F):

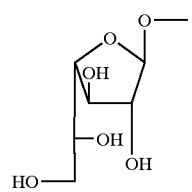

(E)

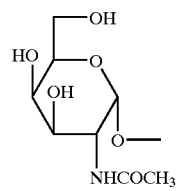

(F)

$R^7$ represents OH or a substituent selected from the group consisting of the following groups (A) to (D):

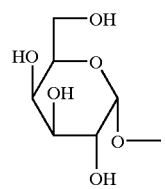

(A)

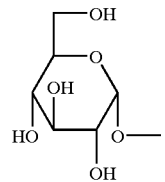

(B)

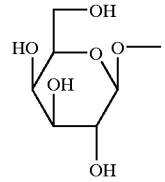

(C)

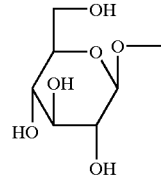

(D)

$R^9$ represents H, $CH_3$, $CH_2OH$ or a substituent selected from the group consisting of the following groups (A') to (D'):

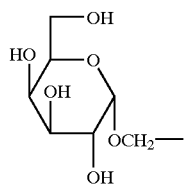
(A')

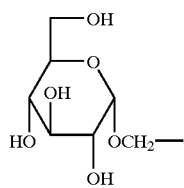
(B')

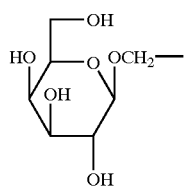
(C')

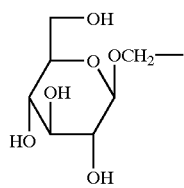
(D')

ii) when $R^3$, $R^6$ and $R^7$ represent H, $R^4$ represents H, OH, $NH_2$, $NHCOCH_3$, or a substituent selected from the group consisting of the following groups (A) to (D):

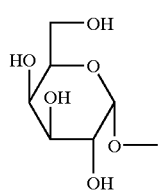
(A)

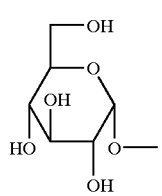
(B)

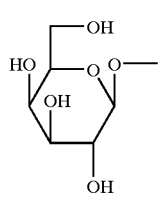
(C)

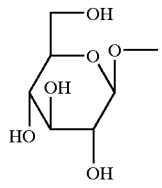
(D)

$R^5$ represents OH or a substituent selected from the group consisting of groups (E) and (F):

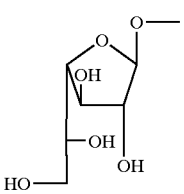
(E)

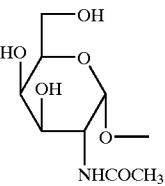
(F)

$R^8$ represents OH or a substituent selected from the group consisting of the following groups (A) to (D):

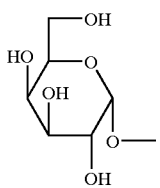
(A)

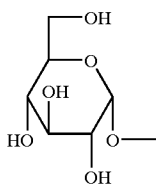
(B)

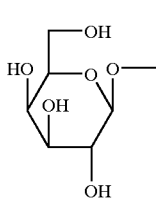
(C)

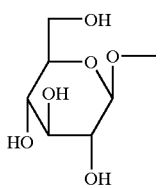
(D)

$R^9$ represents H, $CH_3$, $CH_2OH$ or a substituent selected from the group consisting of the following groups (A') to (D'):

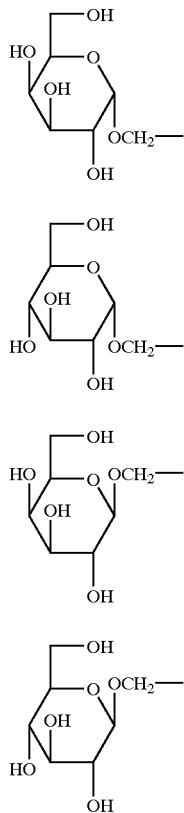

A: Results of FACS analysis of the spleen lymphocyte fraction. The horizontal axis indicates the fluorescence of FITC-labeled anti-TCRαβ monoclonal antibody and the vertical axis indicates the fluorescence of cychrome-labeled anti-NK1.1 monoclonal antibody.

B: Results of FACS analysis of the spleen lymphocyte fraction. The vertical axis indicates relative cell counts and the horizontal axis indicates the fluorescence of PE-labeled Vα14 monoclonal antibody. The white area shows the fluorescence when stained with the PE-labeled Vα14 monoclonal antibody after pretreating with an unlabeled Vα14 monoclonal antibody (cold blocking). The shaded area shows the fluorescence distribution of the PE-labeled Vα14 monoclonal antibody to Vα14⁺ cells after the administration of vehicle or KRN 7000.

C: Change in the number of total cells, T cells, NK cells and Vα14⁺ NKT cells in the spleen lymphocyte fraction by the administration of KRN 7000. ●:Vα14⁺ NKT cells, ○:total cells, ◊:T cells, □:NK cells.

FIG. 3 shows results as to the progression of lymphatic swelling-with time in 1pr/1pr mice to which KRN 7000 was administered. Lymph nodes are scored into 4 grades, i.e., −(0), +(1), ++(2) and +++(3) depending on size. Summed scores of the right and left sides of the axillary lymph node (A) or inguinal lymph node (B) are shown as lymph node swelling indexes.

Figure 4:
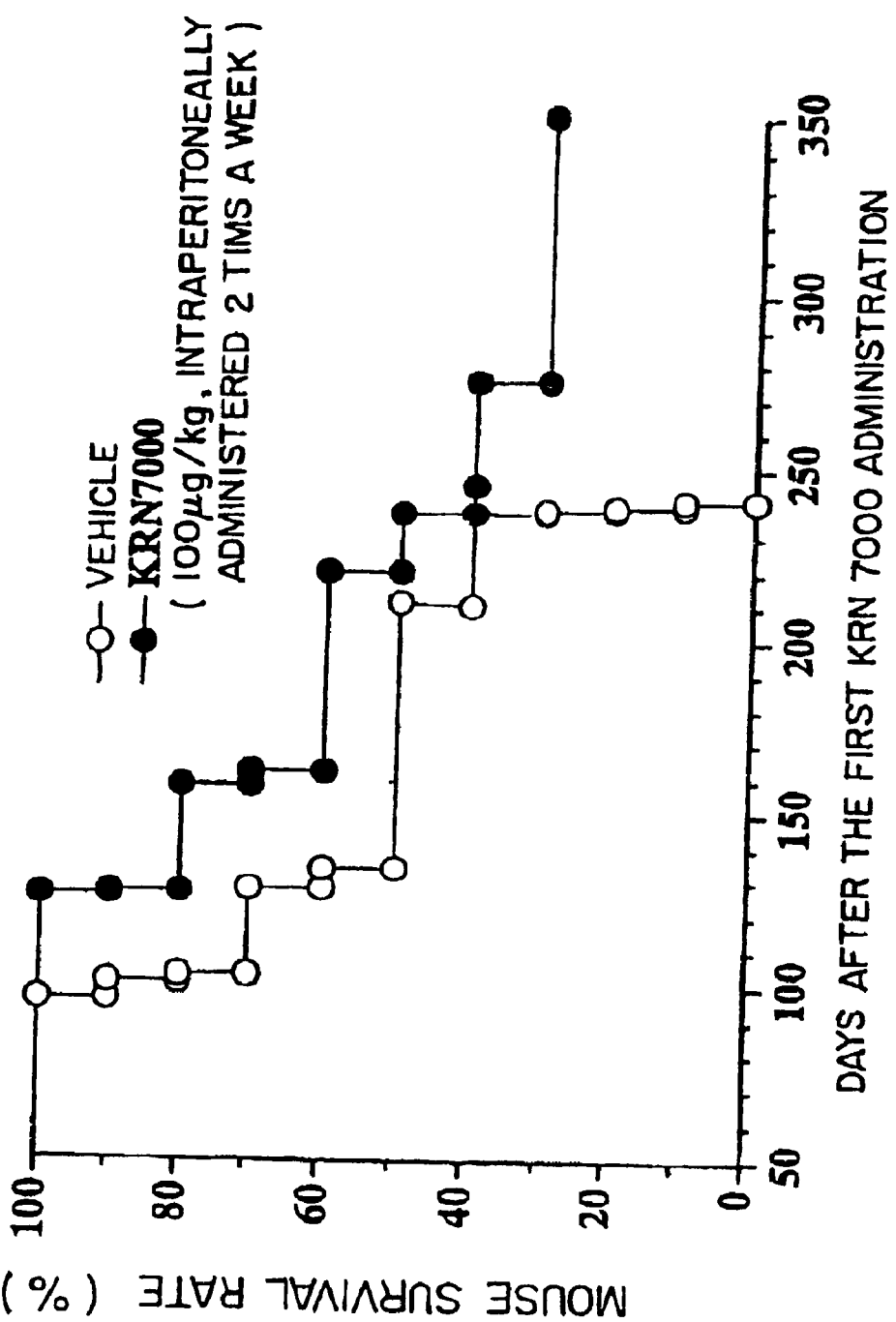

FIG. 4 shows survival rates of MRL lpr/lpr mice to which KRN 7000 was administered.

FIG. 5 shows the activity of KRN 7000 in suppressing colitis in mice induced with 4% DSS. 4% DSS was continuously administered to the mice in the drinking water during the experiment.

A: Change in the body weight of mice in different groups.
B: Survival rates of mice in different groups.

Figure 6:
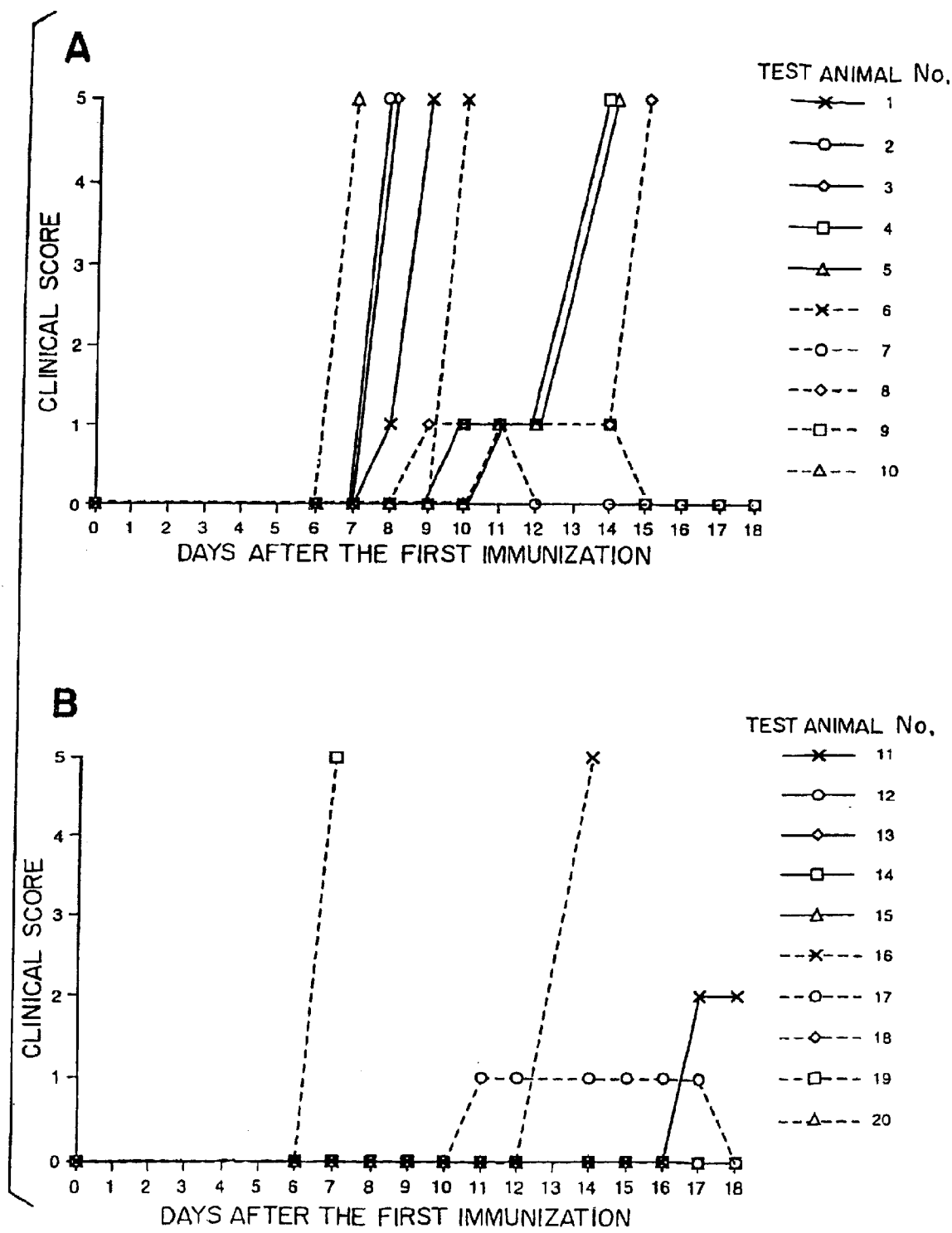

FIG. 6 shows the effect of KRN 7000 on experimental autoimmune encephalomyelitis (EAE) induced in C57BL/6 mice, for example, by myelin oligodendroglia protein (MOG). A: Group to which vehicle was administered. B: Group to which KRN 7000 (20 μg/kg) was administered. EAE symptoms were scored as follows: Clinical scores: 0: normal, 1: paralysis in tails, 2: static reflex insufficiency, 3: paralysis in back feet, 4: paralysis in front and back feet, 5: death.

Figure 7:
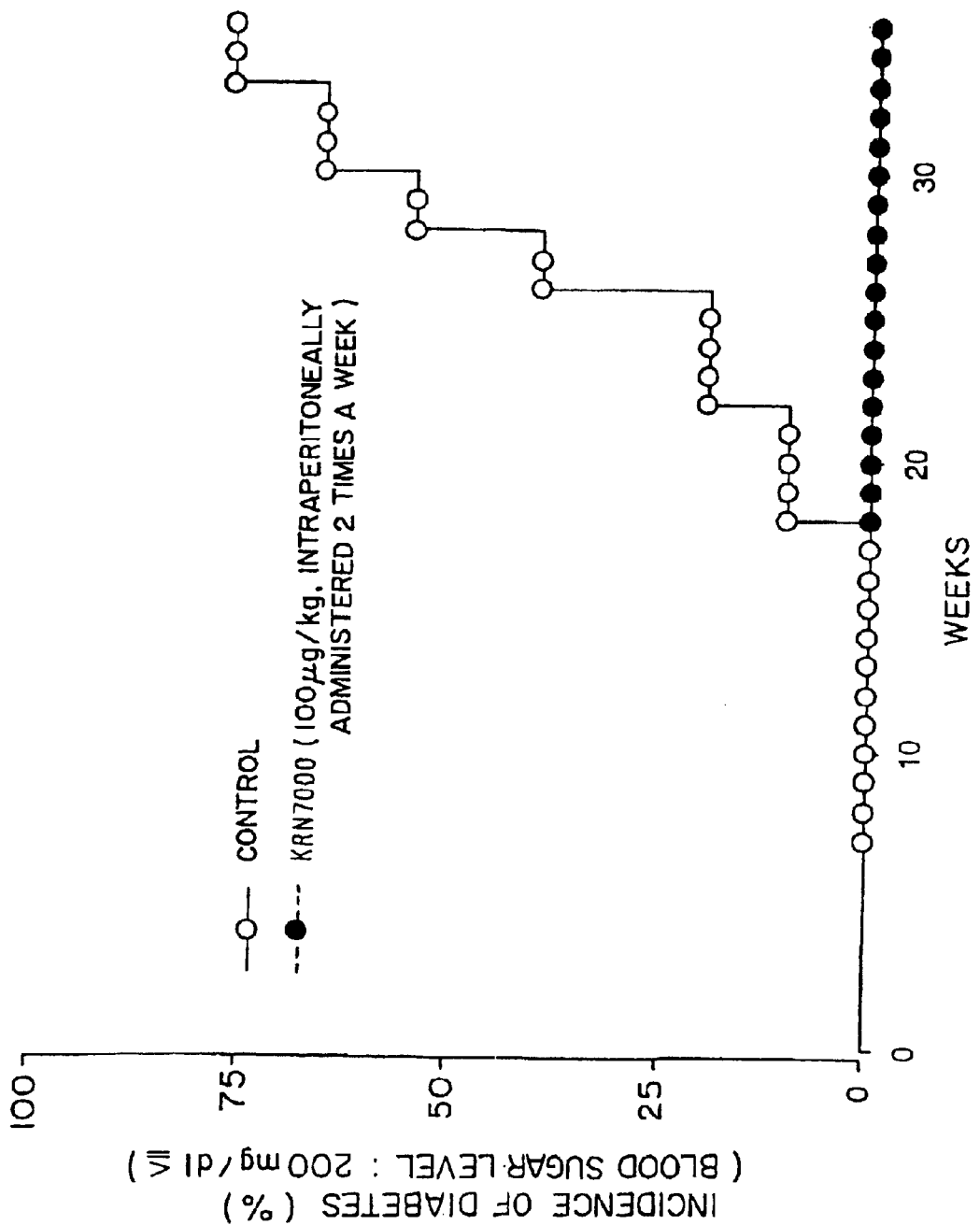

FIG. 7 shows the effect of KRN 7000 on spontaneous diabetes in NOD mice.

Figure 8:
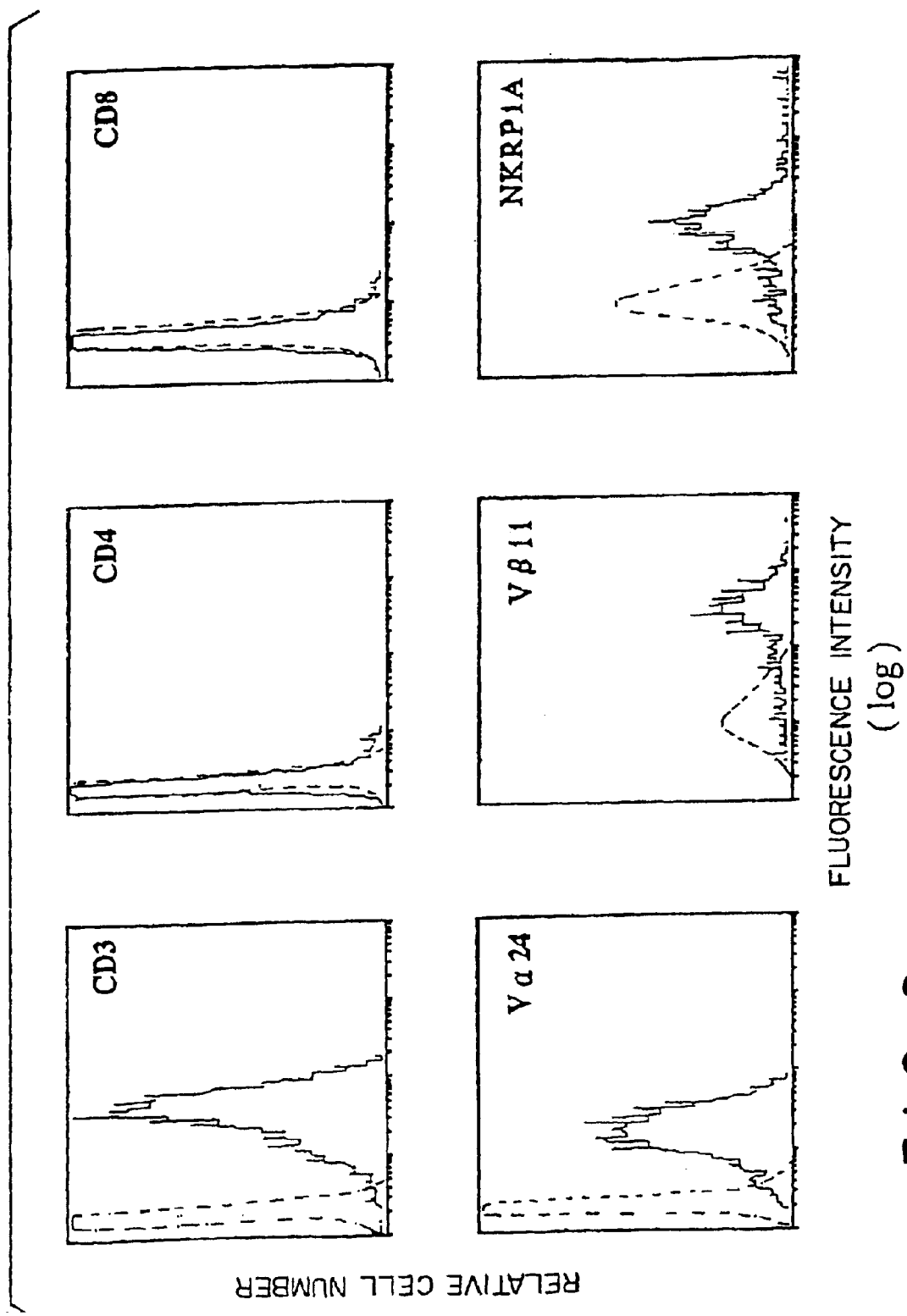

FIG. 8 shows the stimulatory activity of KRN 7000 in the proliferation of Vα24⁺ NKT cells. After an autologous mixed lymphocyte reaction using peripheral blood mononuclear cells as responding cells, CD4⁻CD8⁻ cells were recovered to specify the phenotype using labeled antibodies. Dotted lines indicate the fluorescence distribution when stained with control antibodies (mouse IgG or rat IgM) and solid lines indicate the fluorescence distribution when stained with anti-CD3, CD4, CD8, and Vα24, Vβ11 antibodies (Immunotech), and anti-NKRP1A antibodies (Becton Dickinson).

Figure 9:
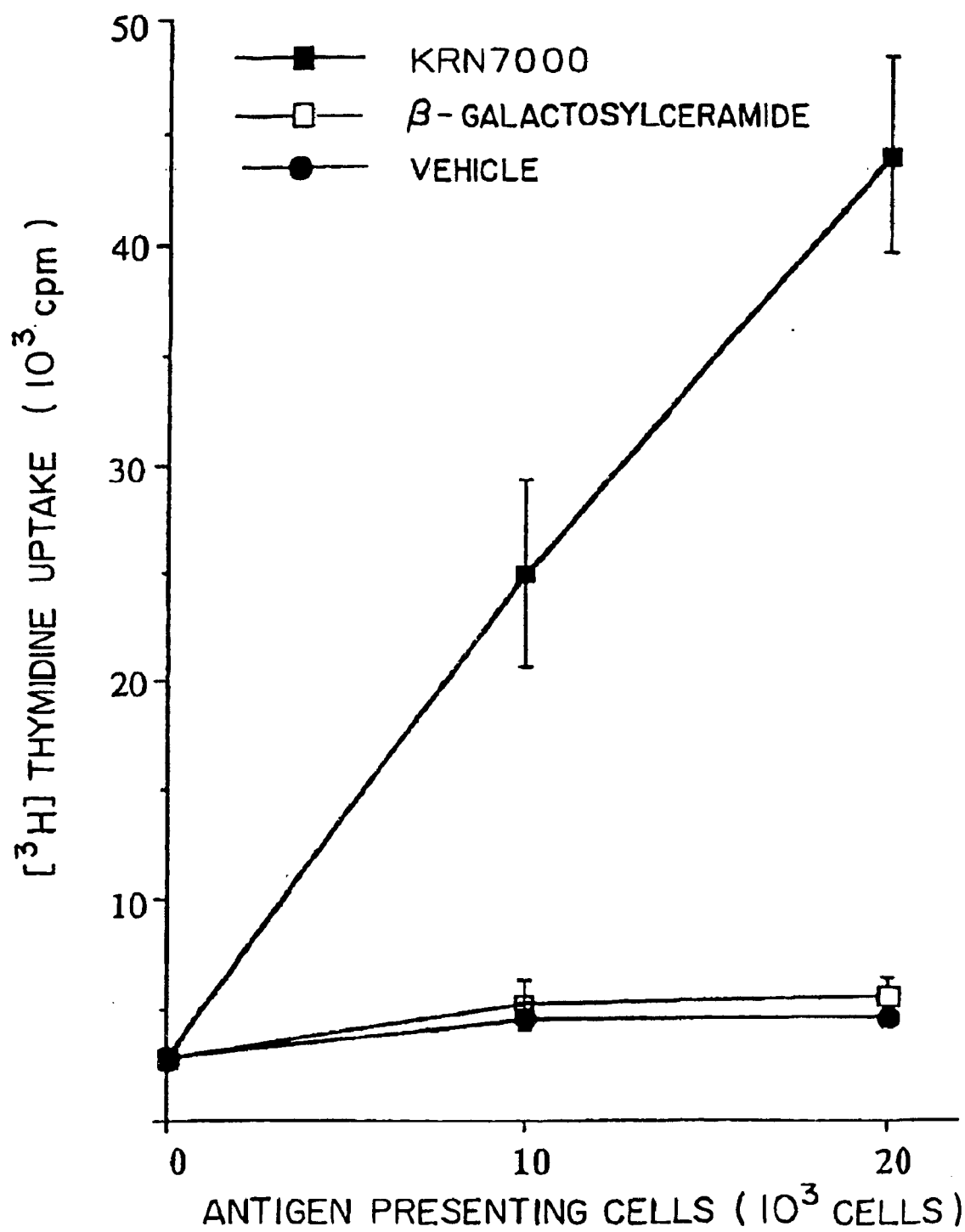

FIG. 9 shows stimulatory activity of KRN 7000 in Vα24⁺ NKT-cell proliferation. When antigen-presenting cells were treated with KRN 7000, stimulation of proliferation of Vα24⁺ NKT cells was observed in a manner dependent on the number of the antigen-presenting cells.

Figure 10:
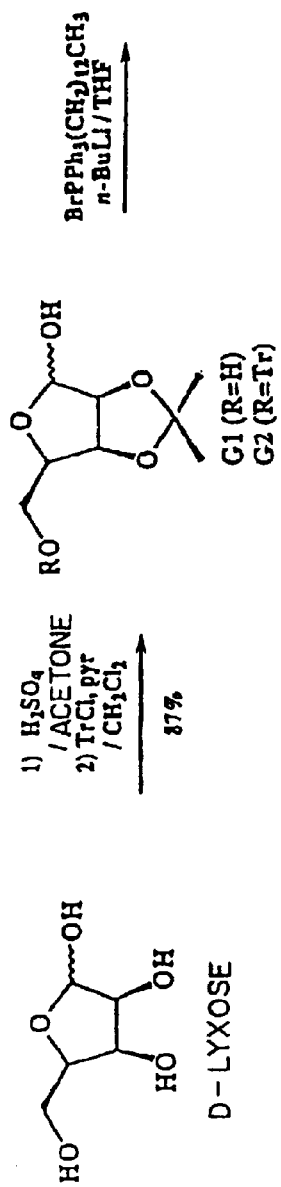
Figure 10:
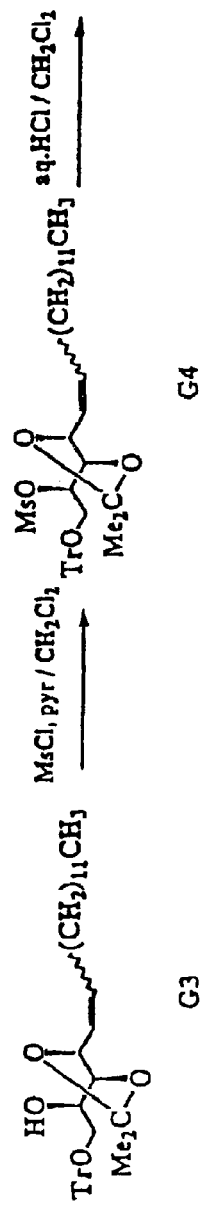
Figure 10:
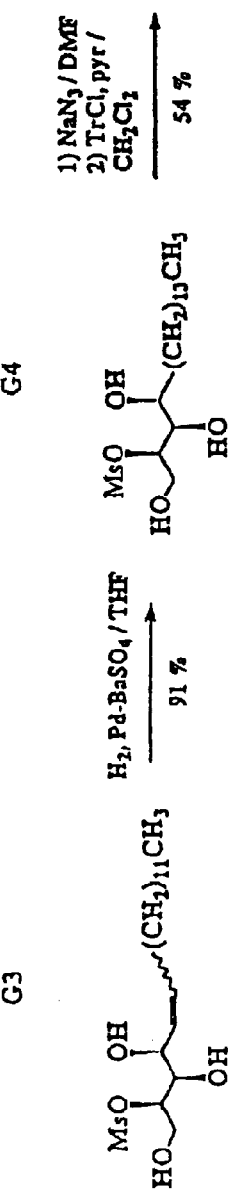
Figure 10:
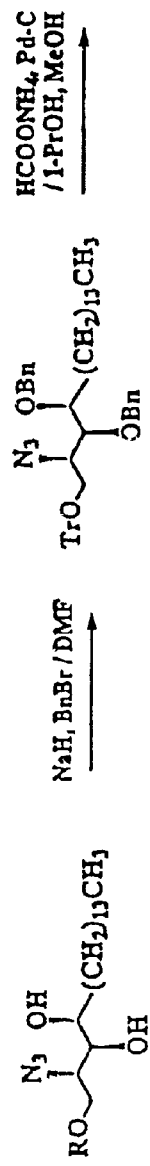
Figure 10:
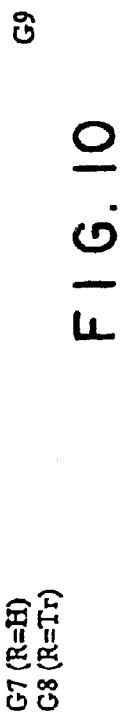

FIG. 10 shows the outline of reactions for the synthesis of KRN 7000, the representative α-glycosylceramide compound used in the present invention. In the drawing, pyr represents pyridine, $BrPPh_3$ $(CH_2)_{12}CH_3$ represents tridecanetriphenylphosphonium bromide, n-BuLi represents n-butyl lithium, MsCl represents methanesulfonyl chloride, BnBr represents benzyl bromide, and 1-PrOH represents propyl alcohol.

Figure 11:
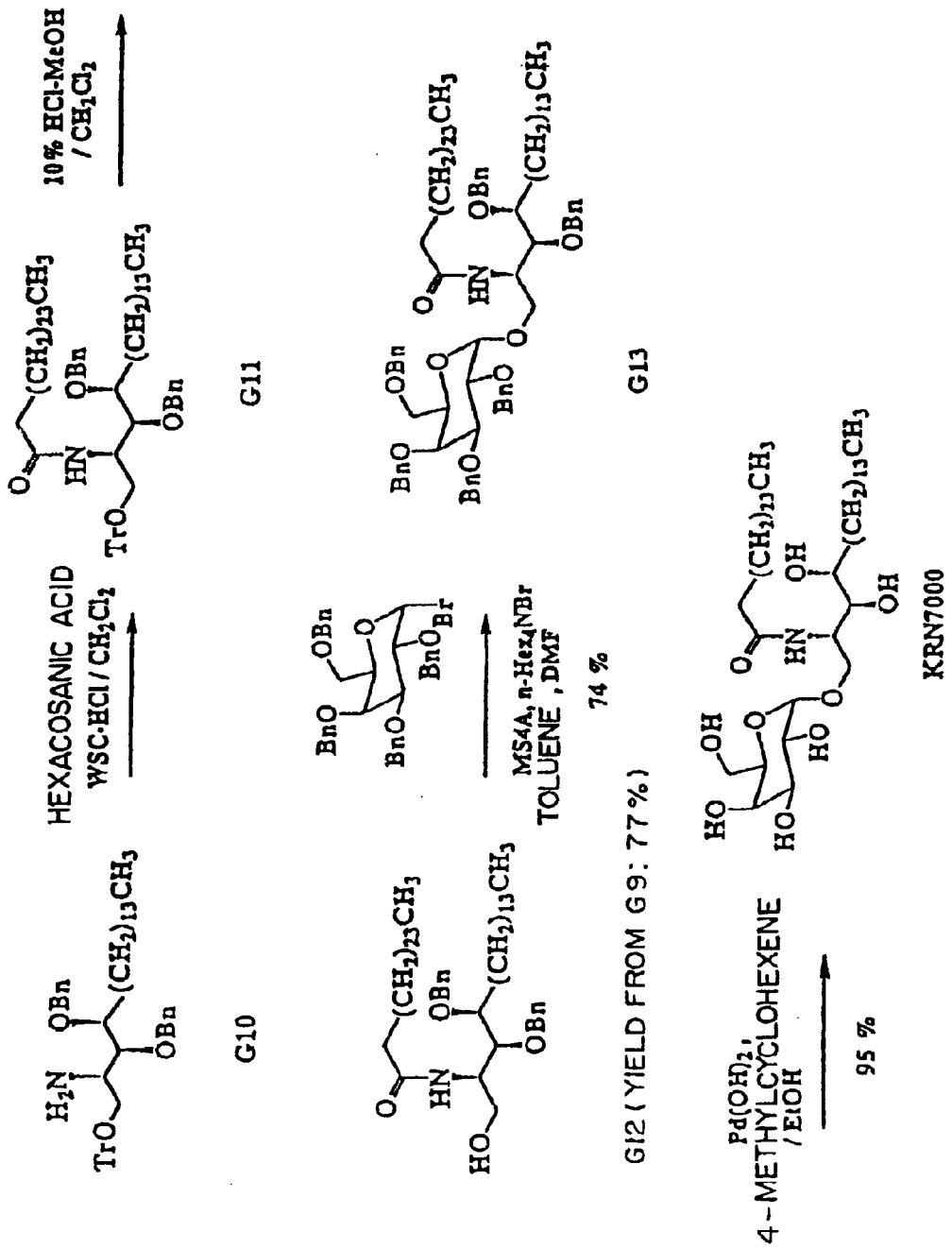

FIG. 11 is the continuation of the reactions for the synthesis as shown in FIG. 10. WSC—HCl represents 1-ethyl-3-(3'-dimethylaminopropyl)-carbodiimide hydrochloride, MS4A represents molecular sieves 4A, and Hex4NBr represents tetrahexylammonium bromide.

Figure 12:
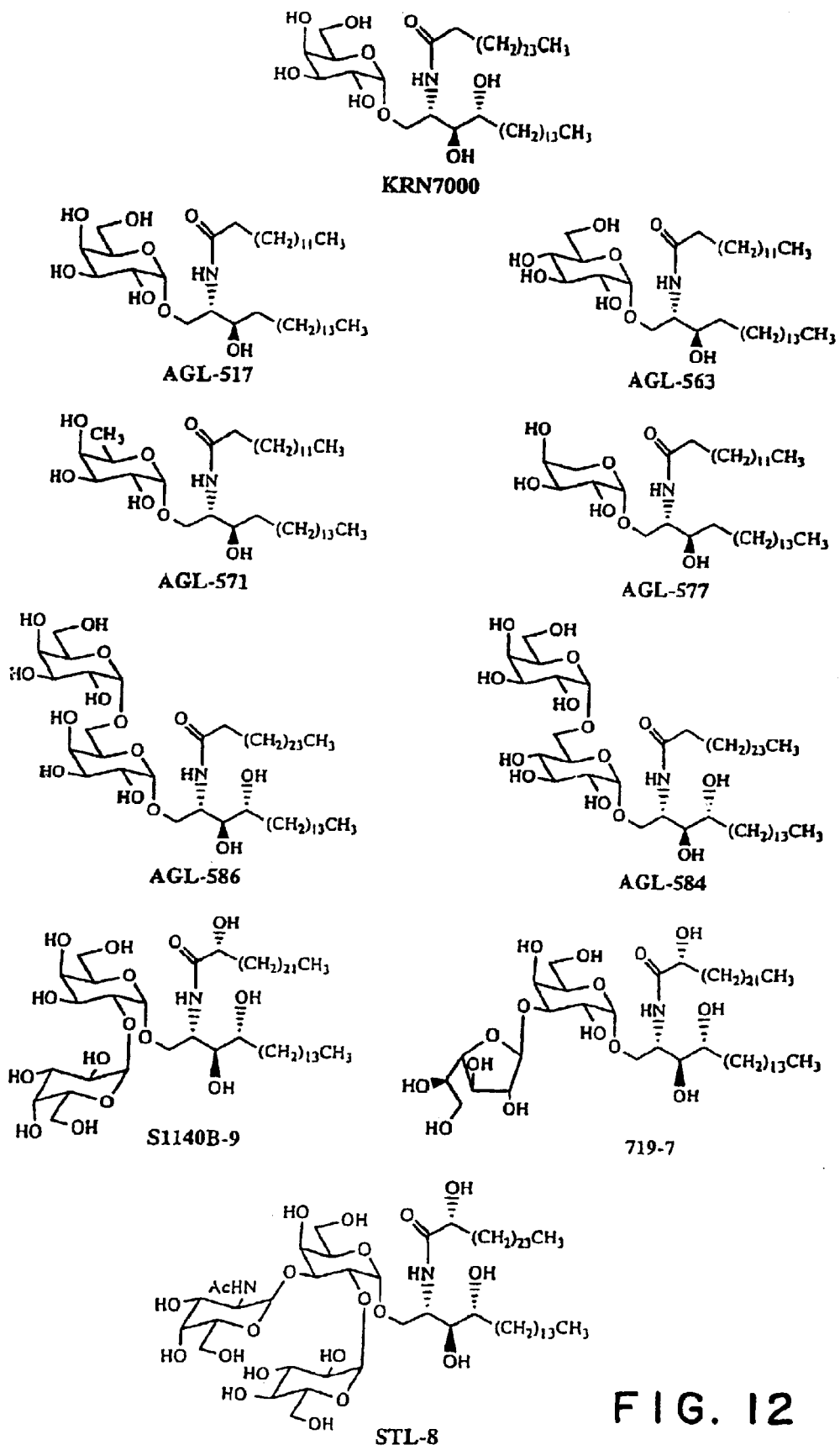

FIG. 12 shows chemical formulas of the compounds in Examples 1 to 3.

DETAILED DESCRIPTION OF THE INVENTION

Compounds of Formula (I)

In the compounds of formula (I), X in the ceramide moiety preferably represents an integer between 11 and 25.

Y in $R^2$ preferably represents an integer between 9 and 17, more preferably between 11 and 15.

Preferable combinations for X and $R^2$ in the ceramide moiety of formula (I) are compounds in which X is an integer between 21 and 25 and $R^2$ is substituent (b) (wherein Y is an integer between 11 and 15) and compounds in which X is an integer between 9 and 13 and $R^2$ is the substituent (a) (wherein Y is an integer between 11 and 15).

Preferable combinations for $R^3$ to $R^9$ in the sugar moiety of formula (I) are compounds in which $R^3$ and $R^6$ are H, $R^4$ is OH or any substituent of groups (A) to (D), $R^5$ is OH or any substituent of group (E) or (F), $R^7$ and $R^8$ are each H or OH (but $R^7$ and $R^8$ are different from one another), and $R^9$ is $CH_2OH$, $CH_3$, H or any substituent of groups (A') to (D').

More preferable combinations include compounds in which $R^3$ and $R^6$ are H, $R^4$ and $R^5$ are OH, $R^7$ and $R^8$ are each H or OH (but $R^7$ and $R^8$ are different from one another), and $R^9$ is $CH_2OH$ or any substituent of groups (A') to (D'), and compounds in which $R^3$, $R^6$ and $R^8$ are H, $R^4$, $R^5$ and $R^7$ are OH, and $R^9$ is $CH_2OH$.

Preferable examples of compounds of formula (I) include compounds in which

X is an integer between 21 and 25, $R^2$ is substituent (b) (wherein Y is an integer between 11 and 15), $R^3$ and $R^6$ are H, $R^4$ is OH or a group selected from the group consisting of groups (A) to (D), $R^5$ is OH or a group selected from the group consisting of groups (E) and (F), $R^7$ and $R^8$ are each H or OH (but both $R^7$ and $R^8$ are not the same substituent), and $R^9$ is $CH_2OH$ or a group selected from the group consisting of groups (A') to (D');

compounds in which

X is an integer between 9 and 13, $R^2$ is substituent (a) (wherein Y is an integer between 11 and 15), $R^3$ and $R^6$ are H, $R^4$ and $R^5$ are OH, $R^7$ and R9 are each H or OH (but both $R^7$ and $R^8$ are not the same substituent), and $R^9$ is H, $CH_3$ or $CH_2OH$;

compounds in which

X is an integer between 21 and 25, $R^2$ is substituent (b) (wherein Y is an integer between 11 and 15), $R^3$ and $R^6$ are H, $R^4$ and $R^5$ are OH, $R^7$ and $R^8$ are each H or OH (but both $R^7$ and $R^8$ are not the same substituent), and $R^9$ is $CH_2OH$ or a group selected from the group consisting of groups (A') to (D'); and compounds in which X is an integer between 21 and 25, $R^2$ is substituent (b) (wherein Y is an integer between 11 and 15), $R^3$, $R^6$ and $R^8$ are H, $R^4$, $R^5$ and $R^7$ are OH, and $R^9$ is $CH_2OH$.

Preferable compounds as effective components of therapeutic agents according to the present invention include (2S,3S,4R)-1-(α-D-galactopyranosyloxy)-2-hexacosanoylamino-3,4-octadecanediol (KRN 7000), (2S,3R)-1-(α-D-galactopyranosyloxy)-2-tetradecanoyl amino-3-octadecanol (AGL-517), (2S,3R)-1-(α-D-glucopyranosyloxy)-2-tetradecanoyl amino-3-octadecanol (AGL-563), (2S,3R)-1-(6'-deoxy-α-D-galactopyranosyloxy)-2-tetra decanoylamino-3-octadecanol (AGL-571), (2S,3R)-1-(β-L-arabinopyranosyloxy)-2-tetradecanoyl amino-3-octadecanol (AGL-577), O-α-D-galactopyranosyl-(1→6)-O-α-D-galactopyranosyl-(1→1)-(2S,3S,4R)-2-amino-N-hexacosanoyl-1,3,4-octa decanetriol (AGL-586), O-α-D-galactopyranosyl-(1→6)-O-α-D-glucopyranosyl-(1→1)-(2S,3S,4R)-2-amino-N-hexacosanoyl-1,3,4-octadecane triol (AGL-584), O-α-D-galactopyranosyl-(1→2)-O-α-D-galactopyranosyl-(1→1)-(2S,3S,4R)-2-amino-N-[(R)-2-hydroxytetracosanoyl]-1,3,4-octadecanetriol (S1140B-9), O-β-D-galactofuranosyl-(1→3)-O-α-D-galactopyranosyl-(1→1)-(2S,3S,4R)-2-amino-N-[(R)-2-hydroxy tetracosanoyl]-1,3,4-octadecanetriol (719-7), and O-(N-acetyl-2-amino-2-deoxy-α-D-galactopyranosyl-(1→3)-O-[α-D-glucopyranosyl-(1→2)]-O-α-D-galacto pyranosyl-(1→1)-(2S,3S,4R)-2-amino-N-[(R)-2-hydroxy tetracosanoyl]-1,3,4-octadecanetriol (STL-8).

A particularly preferable compound used as an active ingredient in therapeutic agents according to the present invention is (2S, 3S, 4R)-1-(α-D-galactopyranosyloxy)-2-hexacosanoylamino-3,4-octadecanediol (KRN 7000).

The compounds of formula (I) may be in the form of pharmaceutically acceptable nontoxic salts thereof. Salts of formula (I) include acid added salts, such as salts with inorganic acids (e.g., hydrochloric acid, sulfuric acid, nitric acid and phosphoric acid) or with organic acids (e.g., acetic acid, propionic acid, maleic acid, oleic acid, palmitic acid, citric acid, succinic acid, tartaric acid, fumaric acid, glutamic acid, pantothenic acid, laurylsulfonic acid, methanesulfonic acid and phthalic acid).

The compounds of formula (I) may be in the form of solvates thereof (e.g., hydrates).

The compounds of formula (I) can be produced by any purposive method to synthesize α-glycosylceramides.

First, a ceramide moiety is synthesized using D-lyxose as a starting material, then a sugar is introduced into this ceramide to prepare compounds of formula (I). A general method to synthesize such α-glycosylceramides can be found, for example, in WO93/5055, WO94/2168, WO/9020 and WO94/24142.

The compounds of formula (I) can also be isolated from natural products (e.g., biological organisms) and purified by column chromatography or the like.

Use of Compounds of Formula (I)

The present inventors have found that antitumor cytotoxic activity of NKT cells against tumor cells was enhanced when KRN 7000, a representative compound according to the present invention, was administered to RAG-1KO/Vα14tg/Vβ8.2tg mice (Pharmacological Test Example 1).

The present inventors have found that α-glycosylceramides markedly increase the number of NKT cells, particularly Vα14⁺ NKT cells and Vα-24⁺ NKT cells (Pharmacological Test Examples 2, 6 and 9). Mouse Vα14⁺ NKT cells and human Vα24⁺ NKT cells have been shown to be involved in various autoimmune diseases caused by different causative genes and genetic background as suggested by findings that Vα-14⁺ NKT cells decrease in autoimmune disease model mice, that Vα24⁺ JαQα T cells disappear in sclerosis patients, and that Vα24⁺ NKT cells greatly decrease in patients with advanced type I diabetes (Mieza, M. A. et al., J. Immunol., 156, 4035 (1996); Makino, Y. et al., Clin. Immunol., 28, 1487 (1996); Sumida, T. et al., J. Exp. Med., 182, 1163 (1995); Wilson et al., Nature, 391, 177 (1998)). The present inventors also found that when KRN 7000 was administered to MRL lpr/lpr mice, which are considered model mice for human systemic lupus erythematosus (Sakamoto, A. Clin. Immunol., 28, 1558 (1996)), abnormal swelling of axillary and inguinal lymph nodes (accumulation of abnormal lymphocytes) was suppressed (Pharmacological Test Example 3). The abnormal swelling of lymph nodes is a characteristic symptom observed in MRL lpr/lpr mice with aging.

Accordingly, as the first aspect of the present invention, the compound of formula (I), or a salt or a solvate thereof can be used as agents for activating NKT cells. "NKT cells" as used herein include human $V\alpha24^+$ NKT cells and mouse $V\alpha14^+$ NKT cells. Human $V\alpha24^+$ NKT cells are a subset of human $V\alpha24J\alpha Q\alpha$ T cells and mean $V\alpha24^+$ double negative ($CD4^-CD8^-$) T cells (Dellabona, P. et al., J.Exp. Med., 180, 1171 (1994)). Furthermore, the term "NKT cell activation" or "activating NKT cell" includes enhancement of cytotoxic activity and stimulation of NKT cell proliferation.

As the second aspect of the present invention, the compound of formula (I), or a salt or a solvate thereof can be used as therapeutic agents for autoimmune diseases. The term "autoimmune diseases" as used herein include systemic lupus erythematosus, systemic sclerosis, ulcerative colitis, multiple sclerosis, encephalomyelitis, type I diabetes, chronic articular rheumatism, Sjoegren's syndrome, primary biliary cirrhosis, idiopathic thrombocytopenic purpura, autoimmune hemolytic anemia, myasthenia gravis, sympathetic ophthalmia, Goodpasture's syndrome (e.g., glomerular nephritis), pernicious anemia, and Hashimoto's disease. The term "treatment" or "therapy" as used herein includes "prevention".

The compound of formula (I) and IL-12 induce abortion in pregnant mice (Pharmacological Test Example 10). Accordingly, as the third aspect of the present invention, the compound of formula (I) or a salt or a solvate thereof and IL-12 can be used as an agent for inducing abortion. The compound of formula (I) and IL-12 can be administered not only to pregnant animals but also to animals that can get pregnant. Pregnancy can be suppressed by administering the compound of formula (I) or IL-12 in advance to animals that can get pregnant. Accordingly, the term "agents for inducing abortion" means "contraceptives".

The compound of formula (I) or a salt or a solvate thereof and IL-12 can be formulated into suitable dosage forms depending on the medical treatment, administration route, and purpose of administration, e.g., injectable agents, suspensions, emulsions, ointments, creams, tablets, capsules, granules, powders, pills, grains, troches, formulations for rectal administration, oily suppositories and water-soluble suppositories.

These various pharmaceutical formulations can be prepared by conventional methods using the following pharmaceutically acceptable vehicles or the like: excipients such as solvents (e.g., water, physiological saline), bulking agents and filling agents (e.g., lactose, starch, crystalline cellulose, mannitol, maltose, calcium hydrogenphosphate, soft silicic acid anhydride and calcium carbonate); auxiliaries such as solubilizing agents (e.g., ethanol and polysolvates), binding agents (e.g., starch, polyvinyl pyrrolidine, hydroxypropyl cellulose, ethylcellulose, carboxymethyl cellulose and gum arabic), disintegrating agents (e.g., starch and carboxymethyl cellulose calcium), lubricating agents (e.g., magnesium stearate, talc and hydrogenated oil), stabilizing agents (e.g., lactose, mannitol, maltose, polysolvates, macrogol, and polyoxyethylene hydrogenated castor oil), isotonic agents, wetting agents, lubricating agents, dispersing agents, buffering agents and solubilizing agents; and additives such as antioxidants, preservatives, flavoring and aromatizing agents, analgesic agents, stabilizing agents, coloring agents and sweetening agents.

If necessary, glycerol, dimethyacetamide, 70% sodium lactate, surfactants and alkaline substances (e.g., ethylenediamine, ethanol amine, sodium carbonate, arginine, meglumine and trisaminomethane) can also be added to various pharmaceutical formulations.

In the present invention, the compound of formula (I) and IL-12 can be administered via any purposive routes, for example, in the case of animals, intraperitoneal or subcutaneous administration, intravenous or intra-arterial administration and local administration by injection. Furthermore, in the case of humans, intravenous or intra-arterial administration, local administration by injection, intraperitoneal or intrathoracic administration, subcutaneous administration, intramuscular administration, sublingual administration, percutaneous absorption or rectal administration can be used. Intravenous administration is most preferable.

Individual effective components in therapeutic agents of the present invention can be administered continuously or intermittently depending on individual situations. Actual doses are determined depending on a variety of factors such as the methods of administration, the conditions of the patient, such as age, body weight, sex and sensitivity, time of administration, and other medicaments taken in combination. A daily dose of compounds of formula (I) and IL-12 for an adult human, for example for intravenous administration, is generally between about 0.001 and 10 mg, preferably between 0.01 and 1 mg. The compound of formula (I) is preferably formulated into freeze-dried preparations, which is preferably dissolved with injection-grade distilled water immediately before administration to patients.

The present invention provides methods of treating autoimmune diseases, which comprises the step of administering NKT cells activated by the compound of formula (I), or a salt or a solvate thereof (activated NKT cells) to mammals, including humans.

Activated NKT cells can be obtained by culturing NKT cells in vitro in the presence of the compound of formula (I), or a salt or a solvate thereof. Furthermore, activated NKT cells can be isolated from the mammal body to which compounds of formula (I) are administered.

NKT cells, which are to be cultured in vitro with compounds of formula (I), can be isolated from healthy humans, patients or suspected sufferers. For human treatment, NKT cells are preferably human $V\alpha24^+$ NKT cells.

Activated NKT cells can be administered to mammals by implanting the activated NKT cells in the animal's body, for example, the vein.

The present invention provides methods for activating NKT cells, which comprise the step of culturing NKT cells in vitro in the presence of a compound of formula (I), or a salt or a solvate thereof.

The present invention provides methods for inducing abortion, which comprise the step of administering the compound of formula (I) or a salt or a solvate thereof, or IL-12 to mammals, including humans.

EXAMPLES

The present invention is further illustrated by the following examples that are not intended as a limitation of the invention.

Synthesis, Isolation and Purification of Compounds

Example 1

Synthesis of (2S,3S,4R)-1-(α-D-galacto pyranosyloxy)-2-hexacosanoylamino-3,4-octadecanediol (KRN 7000)

The synthesizing steps are shown in FIGS. 10 and 11.

(1) Synthesis of Compound G1

Sulfuric acid (0.5 ml) was added to a solution of D-lyxose (200 g, 1.33 mol) in acetone (3.0 L), which had been dried with calcium chloride, and the admixture was stirred for 18 hours at a room temperature. Molecular sieves 4A powder (100 g) was added, the reaction mixture was neutralized, then filtered with Celite, and the resulting residue was washed with acetone. The filtrate and the wash were combined and concentrated under vacuum to obtain a crude product of G1. Yield 240 g (95%). The product was used for the next step without further purification. A sample for assay was purified by silica gel chromatography using hexane:acetone (9:1) as the eluting solvent.

mp76–78° C.; FDMS m/z 191(M+1)$^+$; $^1$H-NMR(500 MHz, CDCl$_3$) δ5.45(1H,d,J=1.8 Hz),4.83(1H,dd,J=3.7,5.5 Hz), 4.64(1H,d,J=6.1 Hz),4.27–4.30(1H,m),3.90–3.99(2H,m), 1.48(3H,s), 1.32(3H,s)

(2) Synthesis of Compound G2

Pyridine (10 ml) and trityl chloride (39.0 g) were added to a methylene chloride solution (168 ml) of compound G1 (239 g, about 1.26 mmol), and the admixture was stirred for 4 hours at 32° C. Ethanol (8 ml) was added dropwise, and the admixture was stirred for 2 hours at a room temperature. After washing with an aqueous saturated ammonium chloride solution, an aqueous saturated sodium hydrogencarbonate solution and a saline solution, concentration under vacuum was carried out. The resulting residue was dissolved in ethyl acetate, cooled to 0° C. and then crystallized. Yield 501 g (87% from D-lyxose).

mp174–176° C.;FDMS m/z 432M$^+$; $^1$H-NMR(500 MHz, CDCl$_3$)δ7.21–7.49(15H,m), 5.38(1H,d,J=2.4 Hz), 4.75 (1H,dd,J=3.7,6.1 Hz), 4.59(1H,d,J=6.1 Hz),4.31–4.35 (1H,m), 3.43(1H,dd,J=4.9, 9.8 Hz),3.39(1H,dd,J=6.7,9.8 Hz), 1.29(3H,s), 1.28(3H,s)

(3) Synthesis of Compound G3

To a THF solution (1500 ml) of tridecanetriphenylphosphonium bromide (962 g, 1.16 mol; prepared by heating 1-bromotridecane and triphenylphosphine for 4.5 hours at 140° C.), a 2.5 M hexane solution of n-butyl lithium (462 ml, 366 mmol) was added dropwise at 0° C. under an argon atmosphere. The admixture was stirred for 15 minutes, then a THF solution (450 ml) of compound G2 (250 g, 579 mmol) was added dropwise. This admixture was stirred for 18 hours while gradually raising the temperature to room temperature. The reaction solution was concentrated under vacuum, a mixture of hexane:methanol:water (10:7:3, 1000 ml) was added to the residue, and the admixture was washed with an aqueous saturated ammonium chloride solution. The water layer was extracted with hexane (500 ml). All the organic layers were combined, dried over anhydrous magnesium sulfate, and then concentrated under vacuum to obtain a crude product of compound G3. The product was used for the next step without further purification. Yield 339 g (98%). A sample for assay was purified by silica gel chromatography using hexane:ethyl acetate (9:1) as the eluting solvent.

FDMS m/z 598M$^+$; $^1$H-NMR(500 MHz,CDCl$_3$)δ7.21–7.45 (15H,m), 5.48–5.59(2H,m),4.91(0.7H,t,J=7.3 Hz),4.44 (0.3H,t,J=7.3 Hz), 4.26(0.3H,dd,J=4.3,7.3 Hz),4.21(0.7H, dd,J=4.3,6.7 Hz), 3.75(0.7H,m),3.69(0.3H,m),3.24(0.3H, dd,J=4.9,9.8 Hz),3.17(0.7H,dd,J=4.9,9.8 Hz),3.09–3.14 [1H,(3.11,dd,J=4.9,9.2 Hz), H1bEoverlapped],1.75–2.03 (2H,m),1.49(3H,s),1.39 and 1.38 (3H,each s),1.21–1.34 (20H,m),0.88(3H,t,J=6.7 Hz)

(4) Synthesis of Compound G4

To a methylene chloride solution (1500 ml) of compound G3 (338 g, about 565 mol), pyridine (500 ml) was added, and methanesulfonyl chloride (49 ml, 633 mmol) was added dropwise. The admixture was stirred for 24 hours at 31° C. Ethanol (40 ml) was added dropwise and the admixture was stirred for 1 hour at a room temperature. After concentration under vacuum, a mixture of hexane:methanol:water (10:7:3, 1000 ml) was added to the residue for separation. The water layer was extracted 3 times with hexane (200 ml). All the organic layers were combined, dried over anhydrous magnesium sulfate, and then concentrated under vacuum to obtain a crude product of compound G4. The product was used for the next step without further purification. Yield 363 g (95%). A sample for assay was purified by silica gel chromatography using hexane:ethyl acetate (9:1) as the eluting solvent.

FDMS m/z 676M$^+$; $^1$H-NMR(500 MHz,CDCl$_3$)δ7.21–7.47 (15H,m), 5.41(0.7H,ddd,J=5.5,9.2,11.0 Hz),5.32(0.7H,bt, J=11.0 Hz),5.22(0.3H,bdd,J=9.2,15.0 Hz),5.02(0.3H,dt, Jt=7.3 Hz,Jd=15.0 Hz), 4.8(0.7H,ddd,J=3.1,5.5,7.9 Hz), 4.73(0.7H,dd,J=5.5,9.8 Hz), 4.64–4.67(0.3H,m),4.61 (0.3H,dd,J=5.5,9.2 Hz), 4.48(0.7H,dd,J=5.5,7.9 Hz),4.22 (0.3H,dd,J=5.5,9.2 Hz), 3.55(0.3H,dd,J=2.4,11.6 Hz), 3.45(0.7H,dd,J=3.2,11.0 Hz), 3.06–3.12[4H,(3.12,s), (3.11,s),(3.09,dd,J=3.1,11.0 Hz)], 1.66–1.82(2H,m),1.47 and 1.46(3H,each s),1.39(3H,s), 1.13–1.35(20H,m),0.88 (3H,t,J=6.8 Hz)

(5) Synthesis of Compound G5

To a methylene chloride solution (1500 ml) of compound G4 (362 g, about 536 mol), methanol (350 ml) was added, then concentrated hydrochloric acid (200 ml) was added dropwise. The admixture was stirred for 5 hours at a room temperature. The reaction solution was neutralized by adding sodium hydrogencarbonate, then filtered. The filtrate was concentrated under vacuum and ethyl acetate was added to the resulting residue and washing was carried out with a saline solution. The water layer was extracted with ethyl acetate, all the organic layers were combined, dried over anhydrous magnesium sulfate, then concentrated under vacuum. Crystallization was carried out with hexane. Yield 161 g (70% from G2).

mp66–67° C.;FDMS m/z 377(M-H$_2$O)$^+$; $^1$H-NMR(500 MHz,CDCl$_3$+D$_2$O) δ5.86(0.3H,dt,Jt=7.3 Hz,Jd=14.7 Hz), 5.77(0.7H,dt,Jt=7.3,Jd=10.4 Hz),5.55(0.3H,br.dd,J=7.3, 14.7 Hz),5.49(0.7H,bt,J=9.8H z),4.91–4.97(1H,m),4.51 (0.7H,bt,J=9.8 Hz),4.11(0.3H,bt, J=7.3 Hz),3.94–4.03 (2H,m),3.67–3.73[1H,(3.70,dd,J=3.1, 6.7 Hz),(3.69,dd,J= 3.1,7.3 Hz)],3.20 and 3.19(3H, each s),2.05–2.22(2H,m), 1.22–1.43(20H,m),0.88(3H,t,J=6.7 Hz)

(6) Synthesis of Compound G6

To a THF solution (780 ml) of compound G5 (160 g, about 405 mol), 5% palladium-barium sulfate (16 g) was added. After replacing the air in a reaction chamber with hydrogen gas, the admixture was stirred for 20 hours at a room temperature. The reaction solution was filtered using Celite, then washed with a mixture of chloroform:methanol (1:1). The filtrate and wash were combined and concentrated under vacuum. The resulting residue was crystallized with ethyl acetate. Yield 146 g (91%).

[α]$^{23}_D$+12° (c1,CHCl$_3$/MeOH=1:1);mp124–126° C;FDMS m/z 397(M+1)$^+$;$^1$H-NMR(500 MHz,CDCl$_3$/CD$_3$OD=1:1) δ4.93–4.96(1H,m, H2),3.91(1H,dd,J=6.7,12.2 Hz),3.85 (1H,dd,J=4.9,12.2 Hz),3.54–3.60(1H,m),3.50 (IH,dd,J= 1.8,8.5 Hz), 3.19 (3H,s),1.75–1.83(1H,m),1.53–1.62(1H, m),1.21–1.45(24H,m),0.89 (3H,t,J=6.7 Hz)

(7) Synthesis of Compound G7

To a DMF solution (1000 ml) of compound G6 (145 g, 365 mol), sodium azide (47 g, 730 mmol) was added, and the admixture was stirred for 4 hours at 95° C. The reaction solution was concentrated, ethyl acetate was added to the resulting residue and washing was carried out with water. The water layer was extracted again with ethyl acetate. All the organic layers were combined, washed with a saline solution, dried over anhydrous magnesium sulfate, and then concentrated under vacuum to obtain a crude product of compound G7. Yield 122 g (97%). The product was used for the next step without further purification. Yield 126 g (95%). A sample for assay was purified by silica gel chromatography using hexane: ethyl acetate (9:1) as the eluting solvent. [α]$^{23}_D$+16.5° (c0.5,CHCl$_3$-MeOH,1:1);mp92–93° C.;FDMS m/z 344(M+1)$^+$;$^1$H-NMR(500 MHz,CD$_3$OD) δ3.91(1H,dd,J=3.7,11.6 Hz), 3.75 (1H,dd,J=7.9,11.6 Hz), 3.49–3.61(3H,m), 1.50–1.71(2H,m), 1.22–1.46(24H,m), 0.90(3H,t,J=6.7 Hz)

(8) Synthesis of Compound G8

To a methylene chloride solution (750 ml) of compound G7 (121 g, about 352 mmol), pyridine (250 ml) and trityl chloride (124 g, 445 mmol) were added, and the admixture was stirred for 16 hours at a room temperature. Ethanol (30 ml) was added dropwise. The admixture was stirred for 30 minutes at a room temperature, washed with an aqueous saturated sodium hydrogencarbonate solution, an aqueous saturated ammonium chloride solution and a saline solution, dried over anhydrous magnesium sulfate, and then concentrated under vacuum. The residue was purified by silica gel chromatography using hexane:ethyl acetate (10:1) as the eluting solvent. Yield 34.4 g (52% from G6).
[α]$^{24}_D$+11.9° (c0.9,CHCl$_3$),FDMS m/z 585M$^+$; $^1$H-NMR (500 MHz,CDCl$_3$+D$_2$O)δ7.24–7.61(15H,m),3.62–3.66 (2H,m), 3.51–3.57(2H,m),3.42(1H,dd,J=6.0,10.4 Hz), 1.23–1.56(26H,m), 0.88(3H,t,J=6.7 Hz)

(9) Synthesis of Compound G9

To a DMF solution (300 ml) of compound G8 (33.5 g, 57.3 mmol), 60% hydrogenated sodium (5.5 g, about 138 mmol as NaH) was added, and the admixture was stirred for 40 minutes at a room temperature. The reaction solution was cooled to 0° C. and benzyl chloride (15 ml, 120 mmol) was added dropwise. The admixture was stirred for 18 hours while gradually raising the temperature to a room temperature. Ice water (100 ml) was added to the reaction solution. After the reaction was stopped, extraction was carried out using ethyl acetate. The extract was washed 3 times with a saline solution, and all the organic layers were combined, dried over anhydrous magnesium sulfate, and then concentrated under vacuum to obtain a crude product of compound G9. The product was used for the next step without further purification. Yield 42.2 g (96%). A sample for assay was purified by silica gel chromatography using hexane:ethyl acetate (100:1) as the eluting solvent.
[α]$^{24}_D$+9.8° (c1.0,CHCl$_3$),FDMS m/z 738(M-N$_2$)$^+$; $^1$H-NMR(500 MHz, CDCl$_3$)δ7.07–7.48(25H,m),4.57 (1H,d,J=11.6 Hz),4.44(1H,d, J=11.6 Hz),4.41(2H,s), 3.73–3.79(1H,m),3.46–3.56(2H,m),3.37 (1H,dd,J=8.6, 10.4 Hz),1.20–1.64(26H,m),0.88(3H,t,J=6.7 Hz)

(10) Synthesis of Compounds G10 and G11

To a 1-propanol solution (250 ml) of compound G9 (41.2 g, about 54 mmol), methanol (30 ml) was added, and further 5% palladium carbon (4.1 g) and ammonium formate (27.1 g, 4.3 mol) were added. After stirring for 16 hours at a room temperature, the admixture was diluted with ethyl acetate and filtered with Celite. The filtrate was concentrated under vacuum, and the resulting residue was dissolved with ethyl acetate and washed 3 times with an aqueous saturated sodium hydrogencarbonate solution and a saline solution. All the organic layers were combined, dried over anhydrous magnesium sulfate, and then concentrated under vacuum to obtain a crude product of G10. Yield 38.9 g (98%). G10 thus obtained was used for the next step without further purification.

To a methylene chloride solution (300 ml) of compound G10, hexacosanoic acid (22.4 g, 56.5 mmol) and WSC hydrogenchloride (12.6 g, 64.6 mmol) were added, and the admixture was fluxed for 2 hours while heating. The mixture was cooled to room temperature and concentrated under vacuum. Ethyl acetate (500 ml) was added to the residue, and washing was carried out with an aqueous 0.5 M hydrochloric acid solution, a saline solution, and an aqueous saturated sodium hydrogencarbonate solution, and further with a saline solution. All the organic layers were combined, dried over anhydrous magnesium sulfate, and then concentrated under vacuum to obtain a crude product of compound G11. Yield 53.2 g (88%). G11 thus obtained was used for the next step without further purification. A sample for assay was purified by silica gel chromatography using hexane-:ethyl acetate (100:1) as the eluting solvent.
[α]$^{24}_D$+5.3° (c0.4,CHCl$_3$);FDMS m/z 1118M$^+$; $^1$H-NMR (500 MHz, CDCl$_3$)δ7.20–7.38(25H,m),5.57(1H,d,J=9.1 Hz),4.80(1H,d, J=11.6 Hz),4.48–4.50(3H,m),4.24–4.32 (1H,m),3.83(1H,dd, J=3.0,6.7 Hz),3.43–3.51(2H,m,H1a), 3.29(1H,dd,J=4.3,9.8 Hz), 1.92(2H,t,J=7.3 Hz), 1.28–1.60(72H,m), 0.88(6H,t,J=6.7 Hz)

(11) Synthesis of Compound G12

To a methylene chloride solution (180 ml) of compound G11 (52.2 g, about 47 mmol), methanol (36 ml) was added, then a 10% methanol chloride solution (3.0 ml) was added dropwise, and the admixture was stirred for 2 hours at a room temperature. The reaction solution was neutralized with sodium hydrogencarbonate powder (18 g) and filtered with Celite. The residue was washed with methylene chloride. The filtrate and wash were combined and washed with a saline solution. The organic layer was dried over anhydrous magnesium sulfate, and then concentrated under vacuum. The residue was dissolved in acetone while heating, and the solution was cooled to 0° C. and purified by precipitation. Yield 38.6 g (77% from G9).
[α]$^{24}_D$−29.7° (c0.7,CHCl$_3$);mp75–76.5° C.;FDMS m/z 876M$^+$; $^1$H-NMR (500 MHz,CDCl$_3$)δ7.30–0.47(10H,m), 6.03(1H,d,J=7.9 Hz),4.72(1H,d,J=11.6 Hz),4.66(1H,d,J= 11.6 Hz),4.61(1H,d,J=11.6 Hz),4.45 (1H,d,J=11.6 Hz), 4.12–4.17(1H,m),4.00(1H,dt,Jt=4.3, Jd=7.3 Hz), 3.67–3.72(2H,m),3.61(1H,ddd,J=4.3,8.6,11.6 Hz), 1.94–2.05(2H,m),1.15–1.69 (72H,m),0.88(6H,t,J=6.1 Hz)

(12) Synthesis of Compound G13

1) 2,3,4,6-tetra-O-benzyl-D-galactopyranosylacetate (79.8 g) was dissolved in a mixture of toluene (160 ml) and isopropyl ether (520 ml), and the solution was cooled to −10 to 0° C. To this solution, an isopropyl ether solution (2.8 mmol/ml, about 100 ml) containing 2.0 equivalent volumes of HBr was added. After stirring for about 90 minutes at −10 to 0° C., an aqueous 5% sodium hydrogencarbonate solution was poured into the reaction solution, and excessive HBr was neutralized by stirring. The whole volume was transferred into a separation funnel for separation, then the water layer was discarded and washing was carried 2 times with an aqueous 10% sodium chloride solution. After concentration under vacuum, 2,3,4,6-tetra-O-benzyl-α-D-galactopyranosyl bromide (GalBr) was obtained as a syrup.

2) DMF (140 ml), then a toluene solution (250 ml) of GalBr (about 137 mmol) were added to a toluene solution (420 ml) of compound G12 (60.0 g, 68.6 mmol), tetrahexylammonium bromide (89.4 g, 206 mmol) and molecular sieves 4A (60 g). The admixture was stirred for 72 hours at a room temperature. Methanol (12 ml) was added to the reaction solution, and the admixture was stirred for 2 hours. Filtration with Celite and washing with an aqueous saturated sodium hydrogencarbonate solution and a saline solution were followed by drying on anhydrous magnesium sulfate and concentration under vacuum. Acetonitrile was added to the resulting residue and the admixture was stirred for 2 hours. The resulting precipitate was dried under vacuum to obtain a dry powder. This powder was purified by silica gel chromatography using hexane:ethyl acetate (8:1) as the eluting solvent. Yield 70.9 g (74%).

$[\alpha]^{24}_D$+18.8° (c0.9,CHCl$_3$);mp74–75° C.;FDMS m/z 1399 (M+1)$^+$; $^1$H-NMR(500 MHz,CDCl$_3$)δ7.21–7.37(30H,m), 6.12(1H,d,J=9.0 Hz),4.91(1H,d,J=11.6 Hz),4.84(1H,d,J=3.7 Hz),4.72–4.80(4H,m),4.35–4.65(7H,m),4.12–4.18 (1H,m),3.99–4.05(2H,m),3.84–3.93(4H,m),3.73(1H,dd, J=3.7, 11.0 Hz),3.47–3.51(2H,m),3.42(1H,dd,J=6.1,9.1 Hz),1.87–1.99 (2H,m),1.18–1.70(72H,m),0.88(6H,t,J= 7.4 Hz)

(13) Synthesis of Compound KRN 7000

Compound G13 (60.0 g, 42.9 mmol) was added to ethanol (960 ml) to make a suspension, to which an ethanol suspension of 20% hydroxy palladium (6.0 g) was added. Further, a hydrogen source, 4-methylcyclohexene (120 ml, 93.5 mmol) was added. After fluxing for 4 hours while heating, filtration was carried out, and the solvent was removed. The residue was washed with heated ethanol. The filtrate was allowed to stand at a room temperature to obtain a white precipitate, and the precipitate was filtered and dried under vacuum. The resulting powder was suspended in ethanol:water (92:8, 3.5 L) and dissolved by heat while stirring. The solution was allowed to stand to obtain a precipitate again. The solution with the precipitate was filtered, and the filtrated cake was dried under vacuum to obtain a white powder. Yield 35.0 g (95%).

$[\alpha]^{23}_D$+43.6° (c1.0,pyridine);mp189.5–190.5° C.; negative FABMS m/z 857(M-H)$^-$;IR(cm$^{-1}$,KBr)3300,2930,2850, 1640,1540, 1470,1070;$^1$H-NMR(500 MHz,C$_5$D$_5$N)δ8.47 (1H,d,J=8.5 Hz), 5.58(1H,d,J=3.7 Hz),5.27(1H,m), 4.63–4.70(2H,m),4.56(1H,m), 4.52(1H,t,J=6.1 Hz), 4.37–4.47(4H,m),4.33(2H,m),2.45(2H,t, J=7.3 Hz), 2.25–2.34(1H,m),1.87–1.97(2H,m),1.78–1.85(2H,m), 1.62–1.72(1H,m),1.26–1.45(66H,m), 0.88(6H,t,J=6.7 Hz),$^{13}$C-NMR(125 MHz,C$_5$D$_5$N)δ173.2(s),101.5(d),76.7 (d),73.0(d),72.5(d),71.6(d),71.0(d),70.3(d),68.7(t),62.7 (t),51.4(d),36.8(t), 34.4(t),32.1(t),30.4(t),30.2(t),30.03(t), 30.00(t),29.93(t),29.87(t),29.81(t),29.76(t),29.6(t),26.5 (t),26.4(t),22.9 (t),14.3(q)

Example 2

Isolation and Purification of O-α-D-galactopyranosyl-(1→2)-O-α-D-galactopyranosyl-(1→1)-(2S,3S,4R)-2-amino-N-[(R)-2-hydroxytetracosanoyl]-1,3,4-octadecanetriol (S1140B-9)

A freeze dried powder (447.1 g) of sponges, which were harvested at a depth of 15–25 m from the sea near Kume Island of Okinawa Prefecture, was extracted with a mixture of chloroform and methanol, then the extracted liquid was concentrated under vacuum to obtain 51.28 g of extract. The extract was partitioned with ethyl acetate and water, and the upper layer and the middle layer were dried over anhydrous sodium sulfate and concentrated under vacuum to obtain 18.37 g and 9.44 g of fractions, respectively. An alcohol layer, which was obtained by partitioning the fraction obtained from the upper layer with 10% aqueous methanol and n-hexane, and the fraction obtained from the middle layer were combined and concentrated. By repeating silica gel chromatography, 169.9 mg of a single active component on normal phase TLC was obtained. Further purification was carried out by reversed phase HPLC using an ODS-AM column (a product of YMC, 250 mm×20 mm diameter, methanol, 9.0 ml/min) (retention time: 30.3 minutes) to obtain 10.2 mg of the purified title compound (S1140B-9).

The title compound can also be isolated and purified by the method described in F. Cafieri et al., Liebigs Ann. Chem. 1995, 1477–1481.

negative FABMS m/z 1007[(M-H)$^-$];IR;$^1$HNMR(500 MHz, C$_5$D$_5$N,24° C.) δ (ppm)8.55(1H,d,J=9.2 Hz,NH),5.60 (1H,d,J=3.7 Hz,H1"),5.57(1H,d,J=3.7 Hz,H1'"),5.13(1H, m,H2),4.75(1H,dd,J=3.7,10.4 Hz, H2"),4.62(2H,m),4.54 (4H,m),4.25–4.47(10H,m),2.17(2H,m),1.99(1H,m),1.87 (2H,m),1.75(1H,m),1.65(2H,m),1.12–1.49(60H,m),0.85 (6H,m,terminal methyl);$^{13}$C NMR(125 MHz,C$_5$D$_5$N,45° C.)δ (ppm)175.5(s,C1'),99.5(d,C1'"),98.6(d,C1"),76.7(d, C2"),76.0(d,C3),72.8(d,C4),72.6(d,C5"), 72.6(d,C4"), 72.5(d,C2),71.3(d,C3'"),71.0(d),70.8(d),70.5(d,C2'"), 69.7(d,C3"),68.6(t,C1),62.7(t),62.5(t),51.2(t, C2),39.4(t), 35.6(t),33.7(t),32.2(t),30.5(t),30.3(t),30.1(t),30.0(t),29.7 (t),29.6(t),26.7(t),26.0(t),23.0(t),22.9(t),14.3(q,terminal methyl)

Example 3

The following compounds were synthesized according to the methods described in the references given on the right column.

| Compound name | Reference |
|---|---|
| (2S, 3R)-1-(α-D-galactopyranosyloxy)-2-tetradecanoylamino-3-octadecanol (AGL-517) | WO93/5055 |
| (2S, 3R)-1-(α-D-glucopyranosyloxy)-2-tetradecanoylamino-3-octadecanol (AGL-563) | WO94/9020 |
| (2S, 3R)-1-(6'-deoxy-α-D-galactopyranosyloxy)-2-tetradecanoylamino-3-octadecanol (AGL-571) | WO94/9020 |
| (2S, 3R)-1-(β-L-arabinopyranosyloxy)-2-tetradecanoylamino-3-octadecanol (AGL-577) | WO94/9020 |
| O-α-D-galactopyranosyl-(1→6)-O-α-D-galactopyranosyl-(1→1)-(2S, 3S, 4R)-2-amino-N-hexacosanoyl-1,3,4-octadecanetriol (AGL-586) | WO94/24142 |
| O-α-D-galactopyranosyl-(1→6)-O-α-D-glucopyranosyl-(1→1)-(2S, 3S, 4R)-2-amino-N-hexacosanoyl-1,3,4-octadecanetriol (AGL-584) | WO94/24142 |
| O-α-D-galactofuranosyl-(1→3)-O-α-D-galactopyranosyl-(1→3)-O-α-D-galactopyranosyl-(1→1)-(2S, 3S, 4R)-2-amino-N-[(R)-2-hydroxytetracosanoyl]-1,3,4-octadecanetriol (719-7) | WO94/24142 |
| O-(N-acetyl-2-amino-2-deoxy-α-D-galactopyranosyl)-(1→3)-O-[α-D-glucopyranosyl-(1→2)]-O-α-D-galactopyranosyl-(1→1)-(2S, 3S, 4R)-2-amino-N-[(R)-2-hydroxytetracosanoyl]-1,3,4-octadecanetriol (STL-8) | WO94/24142 |

Relations between compounds of formula (I) and the compounds described in the example mentioned above are shown in Table 1.

TABLE 1

|  | X | R1 | R2 | R3 | R4 | R5 | R6 | R7 | R8 | R9 |
|---|---|---|---|---|---|---|---|---|---|---|
| KRN7000 | 23 | H | (b)Y = 13 | H | OH | OH | H | OH | H | $CH_2OH$ |
| AGL517 | 11 | H | (a)Y = 13 | H | OH | OH | H | OH | H | $CH_2OH$ |
| AGL563 | 11 | H | (a)Y = 13 | H | OH | OH | H | H | OH | $CH_2OH$ |
| AGL571 | 11 | H | (a)Y = 13 | H | OH | OH | H | OH | H | $CH_3$ |
| AGL577 | 11 | H | (a)Y = 13 | H | OH | OH | H | OH | H | H |
| AGL586 | 23 | H | (b)Y = 13 | H | OH | OH | H | OH | H | Group(A') |
| AGL584 | 23 | H | (b)Y = 13 | H | OH | OH | H | H | OH | Group(A') |
| S1140B-9 | 21 | OH | (b)Y = 13 | H | Group(A) | OH | H | OH | H | $CH_2OH$ |
| 719-7 | 21 | OH | (b)Y = 13 | H | OH | Group(E) | H | OH | H | $CH_2OH$ |
| STL-8 | 23 | OH | (b)Y = 13 | H | Group(B) | Group(F) | H | OH | H | $CH_2OH$ |

Biological Test

Pharmacological Test Example 1

Enhancing Effect of KRN7000 on Cytotoxic Activity of NKT Cells Against Tumor Cells The following experiment was carried out using the compound of Example 1 (KRN 7000) as a representative glycosidic compound of the present invention.

A vehicle (physiological saline containing 0.025% Polysolvate 20) or 100 μg/kg of KRN 7000 was intravenously administered to RAG-1KO/Vα14tg/Vβ8.2tg mice (bearing a large number of NKT cells but not B cells, T cells or NK cells in their lymphocyte fraction), and 24 hours later, the spleen was taken out from each mouse to prepare spleen cells by conventional methods. RAG-1KO/Vα14tg/Vβ8.2tg mice were established by deletion of the RAG-1 gene and forcible expression of Vα14 and Vβ8.2 gene (Kawano T. et al., Science, 278, 1626–1629 (1997)). These mice are available from Masaru Taniguchi, School of Medicine, Chiba University. Cytotoxic activity of these spleen cells to mouse lymphoma YAC-1 cells was studied by the 4 hour-$^{51}$Cr-release method (Kobayashi, E. et al., Oncology Res., 7, 529 (1955)). Results are shown in FIG. 1.

Figure 1:
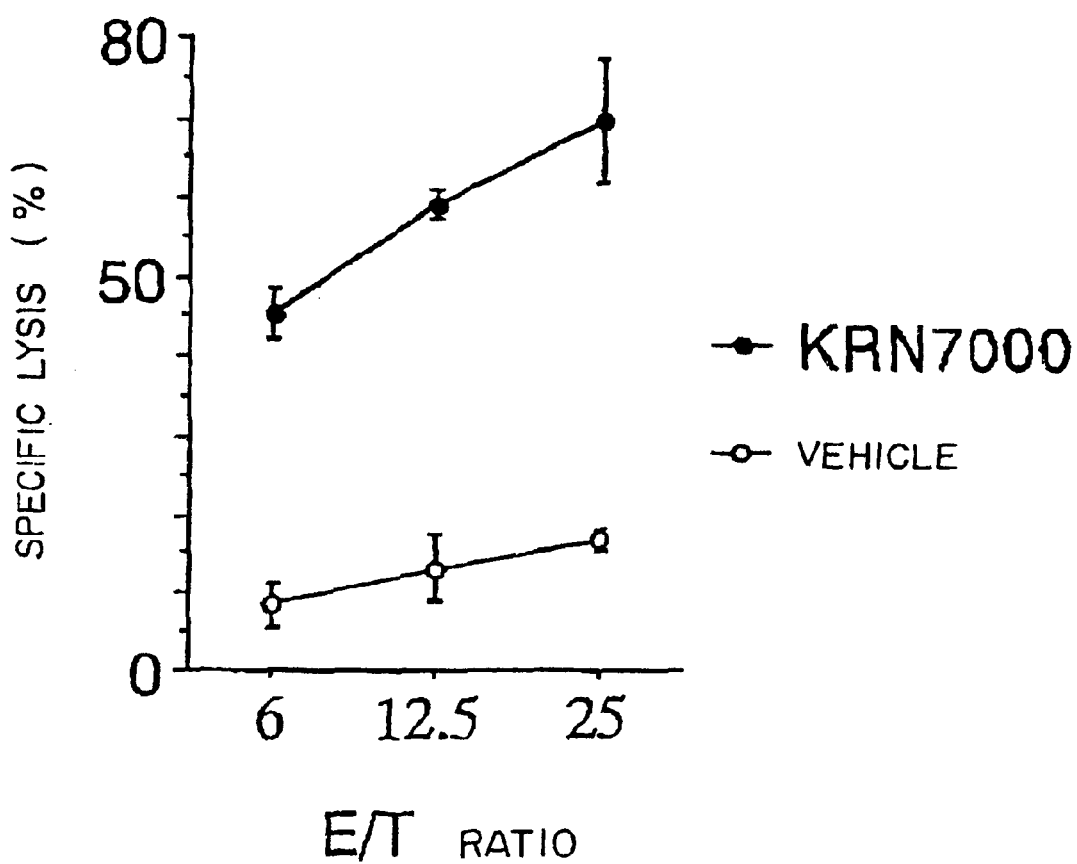
FIG. 1 shows enhancing effect of KRN7000 on cytotoxic activity of NKT cells against tumor cells. The E/T ratio indicates the number of effector cells (spleen cell counts)/the number of target cells (YAC-1 cell counts).

As shown in FIG. 1, cytotoxic activity against YAC-1 cells was significantly higher in the spleen cells prepared from the mice to which KRN 7000 was administered than in those prepared from the mice to which the vehicle was administered.

These results indicate that KRN 7000 enhances cytotoxic activity of spleen NKT cells against tumor cells, considering that RAG-1KO/Vα14tg/β8.2tg mice bear a large number of NKT cells but no B cells, T cells or NK cells in the lymphocyte fraction of the spleen cells.

The results mentioned above indicate that KRN 7000 has an ability to enhance lytic activity of NKT cells against tumor cells.

Pharmacological Test Example 2

Stimulation of Spleen NKT Cell Proliferation by KRN 7000

Figure 2:
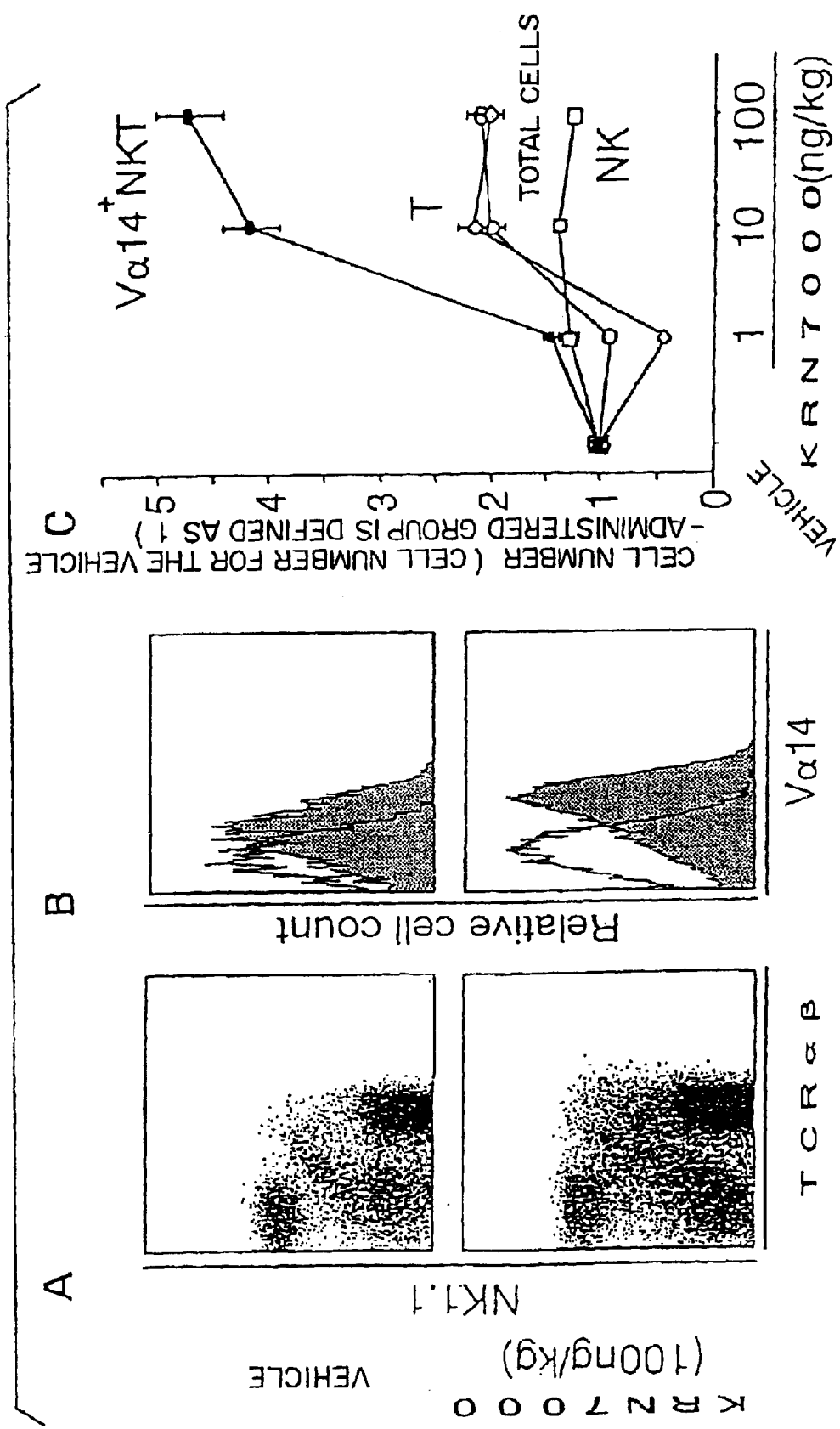
FIG. 2 shows stimulation of NKT cell proliferation by KRN 7000 in the spleen.

A vehicle (physiological saline solution containing 0.5% Polysolvate 20) or 1, 10 or 100 ng/kg of KRN 7000 was intravenously administered to C57BL/6 mice (Japan SLC, Inc.), and the spleen of individual mice was taken out after 24 hours to prepare spleen cells by conventional methods. These spleen cells were incubated in a plastic dish for 30 minutes to prepare nonadherent cells. By removing B cells in this nonadherent cells, a lymphocyte fraction was prepared. T cells, NK cells, NKT cells and Vα14$^+$ NKT cells in this fraction were analyzed by the 3-color FACS analysis using the FITC-labeled anti-TCR αβ monoclonal antibody (Pharmingen), cychrome-labeled anti-NK1.1 monoclonal antibody (Pharmingen) and PE-labeled anti-Vα14 monoclonal antibody (FIG. 2). The anti-Vα14 monoclonal antibody was obtained by implanting anti-Vα14 monoclonal antibody producing hybridomas (CMS-1; available from Masaru Taniguchi et al, School of Medicine, Chiba University) in nude mice and recovering ascites from the animals to purify the antibody. In FIGS. 2A and 2B, the numbers of NK1.1 cells, TCRαβ cells and Vα14 cells in the lymphocyte fraction were expressed as fluorescence intensity of the labeled antibodies against these cells.

As shown in FIG. 2A, a marked increase in the rate of NK1.1$^+$ TCRαβ$^+$ cells in the spleen lymphocyte fraction was observed in animals to which 100 ng/kg of KRN 7000 were administered as compared with animals to which the vehicle was administered.

As shown in FIG. 2B, an increase in the rate of Vα14$^+$ cells in NK1.1$^+$ TCRαβ$^+$ cells was clearly observed in animals to which 100 ng/kg of KRN 7000 was administered as compared with animals to which the vehicle was administered.

Furthermore, as shown in FIG. 2C, the numbers of NK cells in the spleen lymphocyte fractions from the mice to which 10 or 100 ng/kg of KRN 7000 is administered is equal to those from the vehicle-administered mice. However, an about 2-fold increase in the numbers of lymphocyte fractions and T cells was observed in the KRN 7000-administered mice than the vehicle-administered mice. Further, the numbers of Vα14$^-$ NKT cells and Vα14$^+$ NKT cells in the spleen lymphocyte fraction from the KRN 7000-administered mice increased about more than three times (data not shown) and more than four times, respectively, as compared with those from the vehicle-administered mice.

Further, analyses of T cells, NK cells, Vα14$^-$ NKT cells and Vα14$^+$ NKT cells in the liver showed a marked increase in the numbers of Vα14$^-$ NKT cells and Vα14$^+$ cells by KRN7000 administration, similarly to the case of the spleen (data not shown).

The results mentioned above indicate that KRN 7000 has an ability to increase the number of NKT cells, particularly Vα14$^+$ NKT cells, in the body.

Pharmacological Test Example 3

Suppression of Lymph Node Swelling in MRL lpr/lpr Mice by KRN 7000

Ten animals per group of female MRL lpr/lpr mice (Sakamoto, A. Clin. Immunol., 28, 1558 (1966)), were used for the following experiment. During the observation of 21 MRL mice purchased at the age of 6 weeks, swelling of the axillary lymph nodes was recognized in one mouse at the age of 10 weeks. Accordingly, the other 20 mice were randomly divided into 2 groups. A vehicle (a physiological saline solution containing 0.025% Polysolvate 20) or KRN 7000 (100 μg/kg) was intraperitoneally administered twice a week (on Tuesday and Friday) to the abovementioned 2 groups of animals starting from the age of 11 weeks. Axillary and inguinal lymph nodes were examined twice a week to observe the progress of lymph node swelling with time. The lymph nodes were scored into 4 grades, i.e., –(0), +(1), ++(2) and +++(3) as a function of size. The total scores of both right and left sides of the axillary lymph node (A) or inguinal lymph node (B) were expressed as lymph node swelling indexes as shown in FIG. 3.

As shown in FIG. 3A, the swelling in the axillary lymph nodes in MRL mice with aging was clearly suppressed by the administration of KRN 7000. Further, as shown in FIG. 3B, the swelling in the inguinal lymph nodes in MRL mice with aging was also clearly suppressed by the administration of KRN 7000. In other words, KRN 7000 clearly has a capability to suppress lymph node swelling in MRL mice.

The MRL mouse is a model mouse for human systemic lupus erythematosus (Sakamoto, A., Clin. Immun., 28, 1558 (1996)). The results mentioned above indicate that KRN 7000 is effective in treating systemic lupus erythematosus.

Pharmacological Test Example 4

Effect of KRN 7000 on Survival Period of MRL lpr/lpr Mice

Ten animals per group of female MRL lpr/lpr mice were used for the following experiment. MLR mice purchased at the age of 4 weeks were randomly divided into 2 groups (10 animals per group). A vehicle (a physiological saline solution containing 0.025%W Polysolvate 20) or KRN 7000 (100 μg/kg) was intraperitoneally administered twice a week (on Tuesday and Friday) to the animals starting from the age of 5 weeks. Survival of the animals was observed every day.

As shown in FIG. 4, three mice to which KRN 7000 was administered survived even at 350 days after the start of the administration, while all the mice to which the vehicle was administered died within 250 days after the start of the administration.

Pharmacological Test Example 5

Suppression of 4% DSS-Induced Mouse Colitis by KRN 7000

Ten animals per group of CDF1 mice (6 weeks of age, females) (Japan SLC Inc.) were used for the following experiment. Day 0 was defined as the day when a 4% DSS solution (4% (w/v) dextran sodium sulfate (DSS) dissolved in water) was first provided as drinking water. The animals were divided into 3 groups, i.e., a group to which 100 μg/kg of KRN 7000 were intraperitoneally administered on days 1, 5, and 9, a group to which 1 μg/mouse of IL-12 was intraperitoneally administered on days 1, 3, 5, 7 and 9, and an untreated (control) group. Body weight was measured and survival or death of the animals were observed daily. Changes in body weight and survival rate are shown in FIGS. 5A and 5B, respectively.

As shown in FIG. 5A, weight loss was observed at an extremely early period in the IL-12-administered group as compared with the control group. However, weight loss was obviously observed at a later period in the KRN 7000-administered group as compared with the control group.

Furthermore, as shown in FIG. 5B, the survival period of the IL-12-treated mice was significantly shorter than that of the control group. However, the survival period of KRN7000-treated mice was significantly longer than that of the control group.

4% DSS-induced mouse colitis is a model for human ulcerative colitis (Elson, C. et al., Gastroenterology, 109, 1344 (1995)). Accordingly, the results mentioned above indicate that KRN 7000 is effective in treating ulcerative colitis.

Pharmacological Test Example 6

Stimulation of NKT Cell Proliferation by Compounds Having α-Glycosylceramide Structure Stimulation of NKT cell proliferation by compounds having an α-glycosylceramide structure was studied using spleen cells of RAG-1KO/Vα14tg/Vβ8.2tg mice shown in Pharmacological Test Example 1.

Spleen cells were prepared from the spleen of RAG-1KO/Vα14tg/Vβ8.2tg mice by conventional methods. These spleen cells were suspended at $2 \times 10^6$ cells/ml in an RPMI 1640 medium supplemented with 10% FCS, and 100 μl each of the suspension were plated into wells of 96-well round-bottomed plates. Ten different kinds of compounds having an α-glycosylceramide structure shown in FIG. 12 were added to the wells of the plates at a final concentration of 1, 10 or 100 ng/ml, and the plates were incubated for 2 days. Sixteen hours after the addition of [$^3$H] thymidine (0.5 μCi/well), the cells were harvested. The amount of [$^3$H] thymidine incorporated into the cells was measured by a liquid scintillation counter. Results are shown in Table 2.

TABLE 2

| | [$^3$H] Thymidine incorporation (cpm) | | |
|---|---|---|---|
| Sample | 1 (ng/ml) | 10 (ng/ml) | 100 (ng/ml) |
| Vehicle | 2090 | 2056 | 2014 |
| KRN7000 | 40064 | 74669 | 102543 |
| AGL517 | 3176 | 15583 | 83169 |
| AGL563 | 2063 | 3773 | 13131 |
| AGL571 | 3969 | 17848 | 118092 |
| AGL577 | 2083 | 7792 | 49701 |
| AGL586 | 5137 | 39750 | 102425 |
| AGL584 | 29331 | 65084 | 96783 |
| S1140B-9 | 3387 | 10265 | 49520 |
| 719-7 | 5287 | 30179 | 60528 |
| STL-8 | 4761 | 26474 | 47141 |

As shown in Table 2, all the compounds above were revealed to have a significant activity to stimulate NKT cell proliferation at a concentration of 100 ng/ml as compared with the vehicle-added group.

The results mentioned above indicate that glycosidic compounds having an α-D-glycosylceramide and glycosidic compounds having α-D-glycosylceramide, in which other sugar is bound to its sugar moiety, are effective in treating autoimmune diseases.

Pharmacological Test Example 7

Suppression of the Onset of Experimental Autoimmune Encephalomyelitis by KRN 7000

Ten animals per group of C57BL/6 mice (6-week-old females) were used for the following experiment. 200 μg of a partial peptide of myelin oligodendrocyte glycoprotein (MOG33–55) and 500 μg of *Mycobacterium tuberculosis* H37Ra were added to Freund's incomplete adjuvant to prepare an emulsion. Mice were immunized by subcutaneously injecting this emulsion on day 0 and day 7. Further, 500 ng of pertussis toxin were intraperitoneally administered on day 1 and day 2 to induce experimental autoimmune encephalomyelitis (EAE) in mice. The animals were divided into 2 groups, i.e., a group to which 20 μg/kg of KRN 7000 were intraperitoneally administered on days 1, 5, 8, 12 and 15 and a group to which a vehicle (0.5%, Polysolvate 20) was administered in a similar manner. The level of EAE symptoms was observed every day. The level of EAE symptoms of individual mice in each group was shown in FIG. 6.

As shown in FIG. 6, in the vehicle-administered group (FIG. 6A), all the mice showed the EAE onset within 15 days after the first MOG peptide immunization, and 80% of them died. However, in the KRN 7000-administered group (FIG. 6B), 4 out of 10 mice showed the EAE onset, and only 2 of them died.

The results mentioned above indicate that KRN 7000 suppressed the EAE onset in mice. The EAE is a model for human multiple sclerosis (MS) (Autoimmune Disease Models, edited by Cohen I. R. and Miller A., Academic Press, Inc. (1994), Chapter 1, p. 1). Therefore, the results mentioned above indicate that KRN 7000 is effective in treating multiple sclerosis.

Pharmacological Test Experiment 8

Suppression of Mouse Diabetes Onset by KRN 7000

Ten animals per group of NOD/ShiJic (NOD) mice (6-week-old, females) (Japan Clea, Inc.) were used for the following experiment. NOD mice shows the onset of diabetes with aging. The animals were divided into two groups, i.e., one group to which 100 μg/kg of KRN 7000 were intraperitoneally administered twice a week starting from 7-weeks of age, and an untreated control group. The presence and absence of diabetic symptoms was examined every week. The blood glucose level was measured using a glucometer (Miles Sankyo), and mice showing the value of more than 200 mg/dL twice consecutively were diagnosed to be diabetic. FIG. 7 shows the incidence of diabetic mice in the two groups.

As shown in FIG. 7, none of the KRN 7000-administered mice became diabetic even at the age of 35 weeks whereas 80% of the mice in the control group became diabetic at the age of 35 weeks.

The results mentioned above indicate that KRN 7000 suppresses the spontaneous onset of diabetes in NOD mice. The NOC mouse is a model animal for human type I diabetes (Autoimmune Disease Models, edited by Choen I. R. and Miller A., Academic Press, Inc. (1994), Chapter 9, p. 149). The results mentioned above indicate that KRN 7000 is effective in treating type I diabetes.

Pharmacological Test Example 9

Stimulation of Vα24+ NKT Cell Proliferation by KRN 7000

Peripheral blood mononuclear cells of a normal human were cultured for 4 days in an AIM medium supplemented with 10% FCS with the addition of GM-CSF (400 U/ml), IL-4 (200 U/ml) and KRN 7000 (100 ng/ml) to prepare antigen-presenting cells.

An autologous mixed leukocyte reaction (MLR) was performed using these antigen-presenting cells as stimulator cells and autologous peripheral blood mononuclear cells as responder cells. After incubation for 10 days, IL-2 (5 U/ml) was added, incubation was continued for another 4 days, and the cells were harvested. Next, CD4, CD8 double negative cells were recovered from these harvested cells and subjected to the phenotype analysis. The phenotypic analysis was expressed by fluorescence intensity of labeled antibodies against cells having various phenotypes. Results are shown in FIG. 8.

As shown in FIG. 8, it was revealed that a large number of cells having phenotype $CD4^-CD8^-CD3^+V\alpha24^+V\beta11^+NKRP1A^+$ (a subset of $V\alpha24^+$ NKT cells) were present in these cell groups.

The cells were cultured using IL-2 (5 U/ml) to stimulate the proliferation of $V\alpha24^+$ NKT cells, which were used as responder cells in the following autologous mixed leukocyte reaction. Autologous peripheral blood mononuclear cells were cultured for 4 days with the addition of GM-CSF+IL-4 and 100 ng/ml of KRN 7000, AGL-583 (β-galactosylceramide, β-GalCer) or 0.1% DMSO (vehicle) to prepare antigen-presenting cells. An autologous mixed leukocyte reaction was carried out using these antigen-presenting cells as stimulator cells. After incubation for 2 days, [$^3$H]thymidine (0.5 μCi/ml) was added, and cells were harvested after 8 hours to measure [$^3$H]thymidine uptake into the cells by a liquid scintillation counter. Results are shown in FIG. 9.

As shown in FIG. 9, antigen presenting cells treated with the vehicle or β-galactosylceramide showed no effect on $V\alpha24^+$ NKT cell proliferation while antigen presenting cells treated with KRN 7000 showed a marked stimulative effect on $V\alpha24^+$ NKT cell proliferation in a manner dependent on the number of antigen-presenting cells. Furthermore, inhibitory effects of anti-CD1a, CD1b, CD1c, and CD1d antibodies on the stimulation of $V\alpha24^+$ NKT cell proliferation by the KRN 7000-treated antigen-presenting cells were assessed. As a result, only anti-CD1d antibody inhibited the stimulation of $V\alpha24^+$ NKT cell proliferation (data not shown).

The results mentioned above indicate that KRN 7000 is effective in stimulating the proliferation of human $V\alpha24^+$ NKT cells, a counterpart of mouse $V\alpha14^+$ NKT cells. Considering the current report that patients with advanced type I diabetes have an extremely small number of $V\alpha24^+$ NKT cells (Wilson et al., Nature, 391, 177 (1998)) and the results of Pharmacological Test Examples 3, 7 and 8, the results strongly suggest that KRN 7000 is effective in preventing or treating autoimmune diseases, in which human $V\alpha24^+$ NKT cells are involved, such as systemic lupus erythematosus, systemic sclerosis, multiple sclerosis and type I diabetes.

Pharmacological Test Example 10

Induction of Abortion by KRN 7000

C57BL/6 mice (Japan SLC) were used for the following experiment. The day when a vaginal plug was observed was defined as day 0. Pregnant mice were divided into 2 groups (6 mice per group), i.e., one group to which 150 μg/kg of KRN 7000 were intravenously administered on days 7, 8 and 9, and another to which PBS (phosphate- buffered saline) was administered in the same way. On day 12, the uterus was removed to observe the state of the embryo.

In the PBS-administered group, of the total of 53 embryos, 3 were dead and resorbed. The abortion rate was therefore 5.6%. which is consistent with the natural abortion rate of C57BL/6 mice (about 5%).

In the KRN 7000-administered group, of the total of 36 embryos, 12 were dead and resorbed. The abortion rate was 33%, which was obviously higher than that for the untreated group.

When the same amount of KRN 7000 was administered to V$\alpha$14$^+$ NKT-deficient (J$\alpha$281KO) mice (Kawano, T. et al., Science, 278, 1626–1629 (1997)) in the same manner, the abortion rate was 5.3%, which was equivalent to that for the PBS-administered group (5.0%). The V$\alpha$14$^+$ NKT-deficient mice are available from Masaru Taniguchi, School of Medicine, Chiba University.

Considering that KRN 7000 activates NKT cells, a significant correlation between NKT cell activation and abortion induction was indicated.

IL-12 is also known to activate NKT cells. When the same amount of IL-12 was administered to mice ((CBA×DBA/2)F$_1$) in the same manner, the resulting abortion rate was 34%. This result strongly supports the correlation mentioned above.

The results mentioned above indicate that KRN 7000 and IL-12 each have an ability to induce abortion.

Pharmacological Test Example 11

Acute Toxicity Test by a Single Administration

The compound of Example 1 was intravenously administered to mice. Results showed that LD$_{50}$ for the compound was more than 10 mg/kg. Furthermore, the compound has a low toxicity showing no particular symptom at the administration level of 10 mg/kg.

What is claimed is:

1. A method for treating an autoimmune disease comprising the step of administering a compound of formula (I) or a salt or a solvate thereof to a mammal including a human in need thereof:

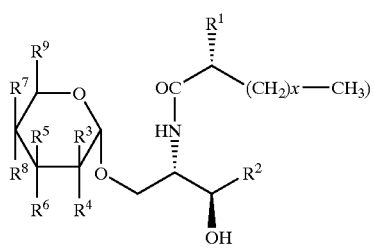

(I)

wherein R$^1$ to R$^9$ and X are as defined wherein
R$^1$ represents H or OH,
X represents an integer between 7 and 27,
R$^2$ represents a substituent selected from the group consisting of the following (a) to (e), wherein Y represents an integer between 5 and 17:
(a) —CH$_2$(CH$_2$)$_y$CH$_3$
(b) —CH(OH)(CH$_2$)$_y$CH$_3$
(c) —CH(OH)(CH$_2$)$_y$CH(CH$_3$)$_2$
(d) —CH=CH(CH$_2$)$_y$CH$_3$
(e) —CH(OH)(CH$_2$)$_y$CH(CH$_3$)CH$_2$CH$_3$, and
R$^3$ to R$^9$ represent substituents as defined in any one of the following (i) to (ii):
(i) when R$^3$, R$^6$ and R$^8$ represent H,
R$^4$ represents H, OH, NH$_2$, NHCOCH$_3$, or a substituent selected from the group consisting of the following groups (A) to (D):

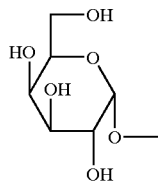
(A)

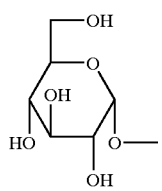
(B)

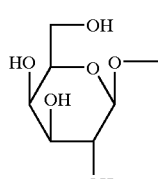
(C)

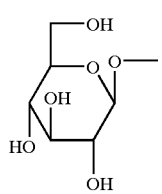
(D)

R$^5$ represents OH or a substituent selected from the group consisting of the following groups (E) and (F):

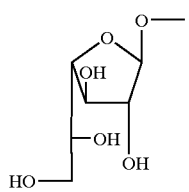
(E)

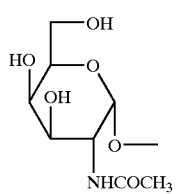
(F)

R$^7$ represents OH or a substituent selected from the group consisting of the following groups (A) to (D):

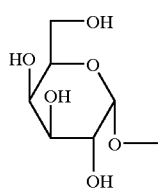
(A)

-continued

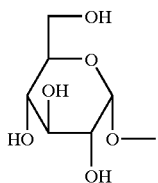
(B)

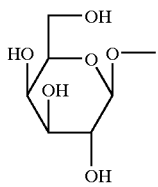
(C)

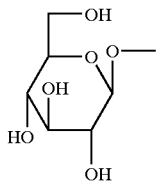
(D)

$R^9$ represents H, $CH_3$, $CH_2OH$ or a substituent selected from the group consisting of the following groups (A) to (D):

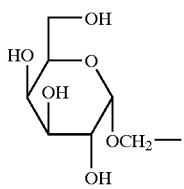
(A′)

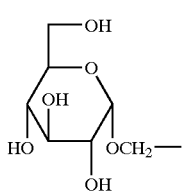
(B′)

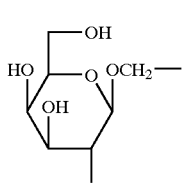
(C′)

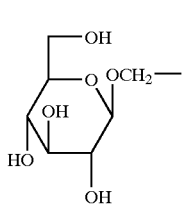
(D′)

(ii) when $R^3$, $R^6$ and $R^7$ represent H, $R^4$ represents H, OH, $NH_2$, $NHCOCH_3$, or a substituent selected from the group consisting of the following groups (A) to (D):

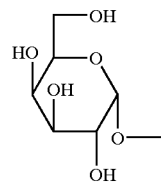
(A)

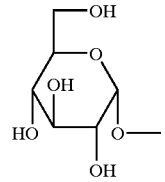
(B)

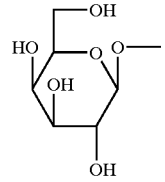
(C)

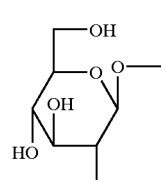
(D)

$R^5$ represents OH or a substituent selected from the group consisting of groups (E) and (F):

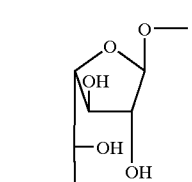
(E)

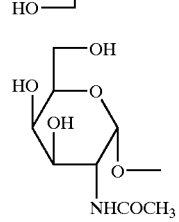
(F)

$R^8$ represents OH or a substituent selected from the group consisting of the following groups (A) to (D):

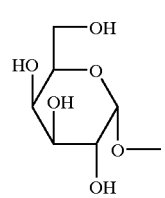
(A)

-continued (B) 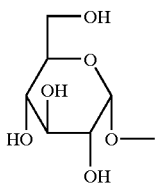

(C) 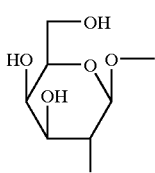

(D) 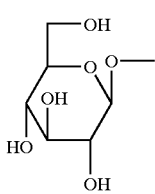

and $R^9$ represents H, $CH_3$, $CH_2OH$ or a substituent selected from the group consisting of the following groups (A) to (D):

(A') 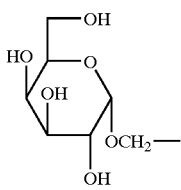

(B') 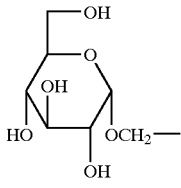

(C') 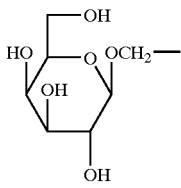

(D') 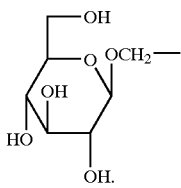

2. A method as claimed in claim 1 wherein the autoimmune disease is systemic lupus erythematosus or systemic sclerosis.

3. A method as claimed in claim 2 wherein $R^3$ and $R^6$ represents H, $R^4$ represents OH or a substituent of any one of groups (A) to (D), $R^5$ represents OH or a substituent of group (F) or (F), $R^7$ and $R^8$ each represent H or OH wherein both $R^7$ and $R^8$ do not represent the same substituent, and $R^9$ represents $CH_2OH$, $CH_3$, H or a substituent of any one of groups (A') to (D').

4. A method as claimed in claim 2 wherein X represents an integer between 21 and 25 and $R^2$ represents substituent (b) wherein Y represents an integer between 11 and 15.

5. A method as claimed in claim 2 wherein X represents an integer between 9 and 13 and $R^2$ represents substituent (a) wherein Y represents an integer between 11 and 15.

6. A method as claimed in claim 2 wherein a compound of formula (I) is (2S,3S,4R)-1-(αD-glactopyransoyloxy)-2-hexacosanoylamino-3,4-octadecanediol.

7. A method as claimed in claim 1 wherein the autoimmune disease is ulcerative colitis.

8. A method as claimed in claim 7 wherein $R^3$ and $R^6$ represents H, $R^4$ represents OH or a substituent of any one of groups (A) to (D), $R^5$ represents OH or a substituent of group (F) or (F), $R^7$ and $R^8$ each represent H or OH wherein both $R^7$ and $R^8$ do not represent the same substituent, and $R^9$ represents $CH_2OH$, $CH_3$, H or a substituent of any on a of groups (A') to (D').

9. A method as claimed in claim 7 wherein X represents an integer between 21 and 25 and $R^2$ represents substituent (b) wherein Y represents en integer between 11 and 15.

10. A method as claimed in claim 7 wherein X represents an integer between 9 and 13 and $R^2$ represents substituent (a) wherein Y represents an integer between 11 and 15.

11. A method as claimed in claim 7 wherein a compound of formula (I) is (2S,3S,4R)-1-(αD-glactopyransoyloxy)-2-hexacosanoylamino-3,4-octadecanediol.

12. A method as claimed in claim 1 wherein the autoimmune disease is encephalomyelitis or multiple sclerosis.

13. A method as claimed in claim 12 wherein $R^3$ and $R^6$ represents H, $R^4$ represents OH or a substituent of any one of groups (A) to (D), $R^5$ represents OH or a substituent of group (B) or (F), $R^7$ and $R^8$ each represent H or OH wherein both $R^7$ and $R^8$ do not represent the same substituent, and $R^9$ represents $CH_2OH$, $CH_3$, H or a substituent of any one of groups (A') to (D').

14. A method as claimed in claim 12 wherein X represents an integer between 21 and 25 and $R^2$ represents substituent (b) wherein Y represents an integer between 11 and 15.

15. A method as claimed in claim 12 wherein X represents an integer between 9 and 13 and $R^2$ represents substituent (a) wherein Y represents an integer between 11 and 15.

16. A method as claimed in claim 12 wherein a compound of formula (I) is (2S,3S,4R)-1-(αD-glactopyransoyloxy)-2-hexacosanoylamino-3,4-octadecanediol.

17. A method as claimed in claim 1 wherein the autoimmune disease is type I diabetes.

18. A method as claimed in claim 17 wherein $R^3$ and $R^6$ represents H, $R^4$ represents OH or a substituent of any one of groups (A) to (D), $R^5$ represents OH or a substituent of group (E) or (F), $R^7$ and $R^8$ each represent H or OH wherein both $R^7$ and $R^8$ do not represent the same substituent, and $R^9$ represents $CH_2OH$, $CH_3$, H or a substituent of any one of groups (A') to (D').

19. A method as claimed in claim 17 wherein X represents an integer between 21 and 25 and $R^2$ represents substituent (b) wherein Y represents an integer between 11 and 15.

20. A method as claimed in claim 17 wherein X represents an integer between 9 and 13 and $R^2$ represents substituent (a) wherein Y represents an integer between 11 and 15.

21. A method as claimed in claim 17 wherein a compound of formula (I) is (2S,3S,4R)-1-(αD-glactopyransoyloxy)-2-hexacosanoylamino-3,4-octadecanediol.

22. A method for inducing abortion which comprises the step of administrating a compound of formula (I) or a salt or a solvate thereof to a mammal including a human in need thereof:

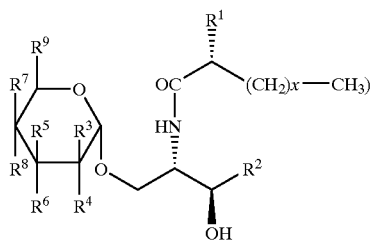
(I)

wherein $R^1$ to $R^9$ and X are as defined wherein $R^1$ represents H or OH,

X represents an integer between 7 and 27, $R^2$ represents a substituent selected from the group consisting of the following (a) to (e), wherein Y represents an integer between 5 and 17:

(a) —$CH_2(CH_2)_yCH_3$
(b) —$CH(OH)(CH_2)_yCH_3$
(c) —$CH(OH)(CH_2)_yCH(CH_3)_2$
(d) —$CH=CH(CH_2)_yCH_3$
(e) —$CH(OH)(CH_2)_yCH(CH_3)CH_2CH_3$, and $R^3$ to $R^9$ represent substituents as defined in any one of the following (i) to (ii):

(i) when $R^3$, $R^6$ and $R^8$ represent H, $R^4$ represents H, OH, $NH_2$, $NHCOCH_3$, or a substituent selected from the group consisting of the following groups (A) to (D):

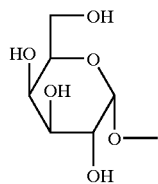
(A)

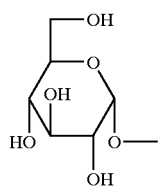
(B)

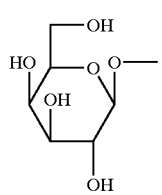
(C)

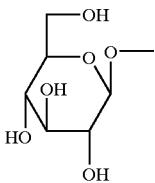
(D)

$R^5$ represents OH or a substituent selected from the group consisting of the following groups (B) and (F):

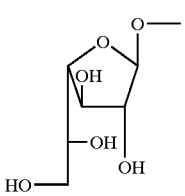
(E)

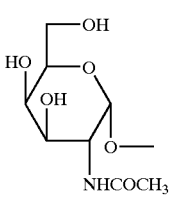
(F)

$R^7$ represents OH or a substituent selected from the group consisting of the following groups (A) to (D):

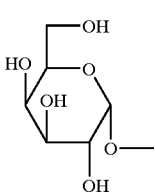
(A)

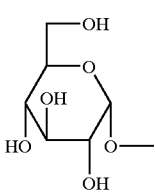
(B)

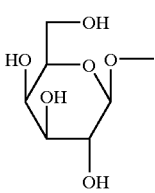
(C)

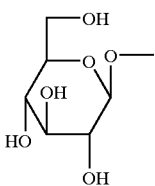
(D)

$R^9$ represents H, $CH_3$, $CH_2OH$ or a substituent selected from the group consisting of the following groups (A) to (D):

(A') 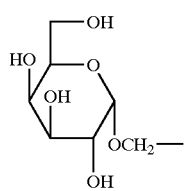

(B') 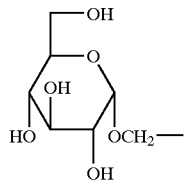

(C') 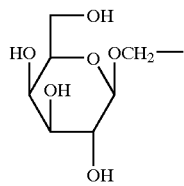

(D') 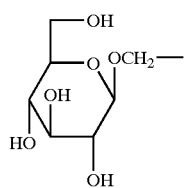

(ii) when $R^3$, $R^6$ and $R^7$ represent H, $R^4$ represents H, OH, $NH_2$, $NHCOCH_3$, or a substituent selected from the group consisting of the following groups (A) to (D):

(A) 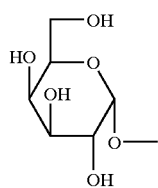

(B) 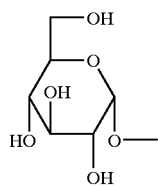

(C) 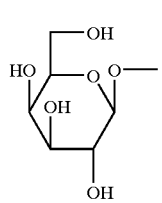

(D) 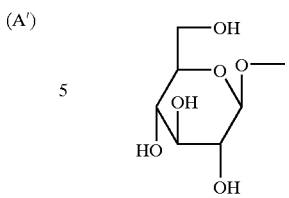

$R^5$ represents OH or a substituent selected from the group consisting of groups (E) and (F):

(E) 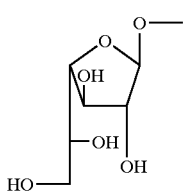

(F) 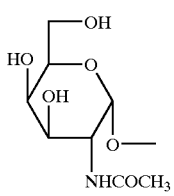

$R^8$ represents OH or a substituent selected from the group consisting of the following groups (A) to (D):

(A) 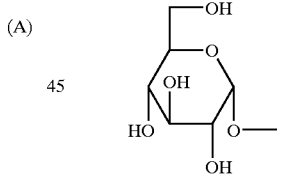

(B) 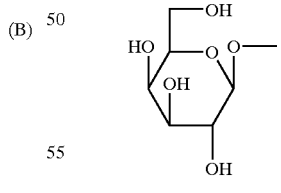

(C) 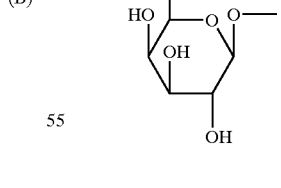

(D) 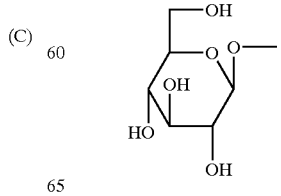

and $R^9$ represents H, $CH_3$, $CH_2OH$ or a substituent selected from the group consisting of the following groups (A) to (D):

(A')
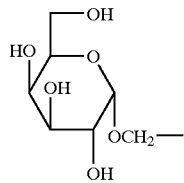

(B')
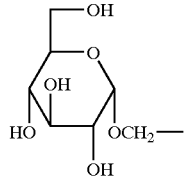

(C')
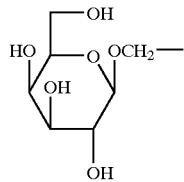

(D')
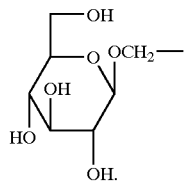

23. A method as claimed in claim 22 wherein $R^3$ and $R^6$ represents H, $R^4$ represents OH or a substituent of any one of groups (A) to (D), $R^5$ represents OH or a substituent of group (F) or (F), $R^7$ and $R^8$ each represent H or OH wherein both $R^7$ and $R^8$ do not represent the same substituent, and $R^9$ represents $CH_2OH$, $CH_3$, H or a substituent of any one of groups (A') to (D').

24. A method as claimed in claim 22 wherein X represents an integer between 21 and 25 and $R^2$ represents substituent (b) wherein Y represents an integer between 11 and 15.

25. A method as claimed in claim 22 wherein X represents an integer between 9 and 13 and $R^2$ represents substituent (a) wherein Y represents an integer between 11 and 15.

26. A method as claimed in claim 22 wherein a compound of formula (I) is (2S,3S,4R)-1-(αD-glactopyransoyloxy)-2-hexacosanoylamino-3,4-octadecanediol.

27. A method as claimed in claim 1 wherein $R^3$ and $R^6$ represents H, $R^4$ represents OH or a substituent of any one of groups (A) to (D), $R^5$ represents OH or a substituent of group (E) or (F), $R^7$ and $R^8$ each represent H or OH wherein both $R^7$ and $R^8$ do not represent the same substituent, and $R^9$ represents $CH_2OH$, $CH_3$, H or a substituent of any one of groups (A') to (D').

28. A method as claimed in claim 1 wherein X represents an integer between 21 and 25 and $R^2$ represents substituent (b) wherein Y represents an integer between 11 and 15.

29. A method as claimed in claim 1 wherein X represents an integer between 9 and 13 and $R^2$ represents substituent (a) wherein Y represents an integer between 11 and 15.

30. A method as claimed in claim 1 wherein a compound of formula (I) is (2S,3S,4R)-1-(α-D-galactopyranosyloxy)-2-hexacosanoylamino-3,4-octadecanediol.

* * * * *